US009770040B2

(12) United States Patent
Gutzmann et al.

(10) Patent No.: US 9,770,040 B2
(45) Date of Patent: *Sep. 26, 2017

(54) TREATMENT OF ANIMAL CARCASSES

(71) Applicant: Ecolab USA Inc., St. Paul, MN (US)

(72) Inventors: Timothy A. Gutzmann, Eagan, MN (US); Brian J. Anderson, Robbinsdale, MN (US); Pamela J. Reed, St. Paul, MN (US); Bruce R. Cords, Inver Grove Heights, MN (US); Lawrence A. Grab, Woodbury, MN (US); Edward H. Richardson, Columbia Heights, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,931

(22) Filed: Nov. 10, 2016

(65) Prior Publication Data
US 2017/0094985 A1 Apr. 6, 2017

Related U.S. Application Data

(60) Continuation of application No. 13/216,133, filed on Aug. 23, 2011, now Pat. No. 9,560,875, which is a continuation of application No. 11/894,334, filed on Aug. 20, 2007, now Pat. No. 8,030,351, which is a continuation of application No. 10/370,798, filed on Feb. 20, 2003, now Pat. No. 8,043,650, which is a continuation of application No. 10/084,697, filed on Feb. 28, 2002, now Pat. No. 6,545,047, which is a continuation of application No. 09/634,502, filed on Aug. 9, 2000, now abandoned, which is a division of application No. 09/419,019, filed on Oct. 15, 1999, now Pat. No. 6,103,286, which is a division of application No. 09/137,242, filed on Aug. 20, 1998, now Pat. No. 6,010,729.

(51) Int. Cl.
| | |
|---|---|
| *A01N 37/00* | (2006.01) |
| *A23B 4/023* | (2006.01) |
| *A23B 4/12* | (2006.01) |
| *A23B 4/30* | (2006.01) |
| *A23L 3/3508* | (2006.01) |
| *A01N 37/16* | (2006.01) |
| *A01N 37/02* | (2006.01) |
| *A01N 59/00* | (2006.01) |

(52) U.S. Cl.
CPC .......... *A23B 4/12* (2013.01); *A01N 37/02* (2013.01); *A01N 37/16* (2013.01); *A01N 59/00* (2013.01); *A23B 4/30* (2013.01); *A23L 3/3508* (2013.01); *A23V 2002/00* (2013.01)

(58) Field of Classification Search
CPC ........ A01N 37/00; A01N 37/02; A01N 37/16; A23L 3/3508; A23L 3/3517
USPC .......................................... 514/557; 426/652
See application file for complete search history.

(56) References Cited

U.S. PATENT DOCUMENTS

| | | | |
|---|---|---|---|
| 1,750,657 A | 3/1930 | Adolph et al. |
| 2,512,640 A | 6/1950 | Greenspan et al. |
| 2,590,856 A | 4/1952 | Greenspan et al. |
| 2,609,391 A | 9/1952 | Greenspan et al. |
| 2,673,804 A | 3/1954 | Paddock |
| 2,735,777 A | 2/1956 | Meyer |
| 2,833,813 A | 5/1958 | Wallace |
| 2,910,504 A | 10/1959 | Hawkinson et al. |
| 2,919,283 A | 12/1959 | Greenspan et al. |
| 2,966,415 A | 12/1960 | Rinehart et al. |
| 3,122,417 A | 2/1964 | Blaser et al. |
| 3,130,207 A | 4/1964 | Greenspan et al. |
| 3,140,312 A | 7/1964 | Kurhajec et al. |
| 3,248,281 A | 4/1966 | Goodenough |
| 3,251,862 A | 5/1966 | Lidov |
| 3,350,265 A | 10/1967 | Rubinstein et al. |
| 3,514,278 A | 5/1970 | Brink |
| 3,895,116 A | 7/1975 | Herting et al. |

(Continued)

FOREIGN PATENT DOCUMENTS

| | | |
|---|---|---|
| AU | 199943467 | 3/2000 |
| AU | 758625 | 3/2003 |
| CA | 2181416 | 1/1997 |
| CA | 2351259 | 12/2001 |
| CA | 2280307 | 9/2004 |
| DE | 30 03 875 | 8/1981 |
| DE | 35 43 500 | 6/1987 |
| DE | 39 06 044 | 8/1990 |
| DE | 281 119 | 8/1990 |
| DE | 197 51 391 | 7/1998 |

(Continued)

OTHER PUBLICATIONS

Abstract: "Indirect food additives: adjuvants, production aids, and sanitizers", Fed. Register, 61(108), 28051-28053, 1 pg. (Jun. 4, 1996).
Agner and Theorell, Arch. Biochem. (1946) 10:321-338.
Armak Chemicals, "NEO-Fat Fatty Acids", Akzo Chemicals Inc., Bulletin No. 86-17 (1986).
Baldry et al., Wat. Sci. Tech. (1989) 21(3):203-206.
Baldry et al., "Disinfection with peroxygens," Industrial Biocides, edited by K.R.Payne, New York, John Wiley & Sons, pp. 91-116 (1988).

(Continued)

Primary Examiner — Kevin E Weddington
(74) Attorney, Agent, or Firm — Morrison & Foerster LLP

(57) ABSTRACT

Described is a method of sanitizing animal carcasses using aqueous streams having an antimicrobial composition added to the stream. Preferably, the antimicrobial composition includes a mixture of one or more carboxylic acids having up to 18 carbon atoms and one or more peroxycarboxylic acids having up to 12 carbon atoms, preferably a mixture of a $C_2$-$C_4$ peroxycarboxylic acid and a $C_8$-$C_{12}$ peroxycarboxylic acid. Also described is a novel antimicrobial composition adapted for sanitizing animal carcasses containing a mixture of one or more $C_2$-$C_4$ peroxycarboxylic acids and one or more $C_8$-$C_{12}$ peroxycarboxylic acids and an alpha-hydroxy mono- or dicarboxylic acid.

30 Claims, No Drawings

(56) References Cited

U.S. PATENT DOCUMENTS

| | | |
|---|---|---|
| 3,929,678 A | 12/1975 | Laughlin et al. |
| 3,934,044 A | 1/1976 | Busch et al. |
| 3,996,386 A | 12/1976 | Malkki et al. |
| 4,013,575 A | 3/1977 | Castrantas et al. |
| 4,026,798 A | 5/1977 | Castrantas et al. |
| 4,041,149 A | 8/1977 | Gaffar et al. |
| 4,051,058 A | 9/1977 | Bowing et al. |
| 4,051,059 A | 9/1977 | Bowing et al. |
| 4,097,520 A | 6/1978 | Slattery |
| 4,115,410 A | 9/1978 | Watts |
| 4,129,517 A | 12/1978 | Eggensperger et al. |
| 4,130,501 A | 12/1978 | Lutz et al. |
| 4,137,256 A | 1/1979 | Slattery et al. |
| 4,172,086 A | 10/1979 | Berkowitz |
| 4,191,660 A | 3/1980 | Schreiber et al. |
| 4,196,221 A | 4/1980 | Dew |
| 4,244,884 A | 1/1981 | Hutchins et al. |
| 4,289,728 A | 9/1981 | Peel et al. |
| 4,297,298 A | 10/1981 | Crommelynck et al. |
| 4,370,199 A | 1/1983 | Orndorff |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,566,980 A | 1/1986 | Smith |
| 4,590,286 A | 5/1986 | Bull |
| 4,591,565 A | 5/1986 | Branner-Jorgensen et al. |
| 4,592,488 A | 6/1986 | Simon et al. |
| 4,613,452 A | 9/1986 | Sanderson |
| 4,618,914 A | 10/1986 | Sato et al. |
| 4,650,612 A | 3/1987 | Dankowski |
| 4,655,781 A | 4/1987 | Hsieh et al. |
| 4,659,494 A | 4/1987 | Soldanski et al. |
| 4,666,622 A | 5/1987 | Martin et al. |
| 4,683,618 A | 8/1987 | O'Brien |
| 4,704,404 A | 11/1987 | Sanderson |
| 4,715,980 A | 12/1987 | Lopes et al. |
| 4,738,840 A | 4/1988 | Simon et al. |
| 4,743,447 A | 5/1988 | Le Rouzic et al. |
| 4,766,646 A | 8/1988 | Parker |
| 4,770,884 A | 9/1988 | Hill et al. |
| 4,802,994 A | 2/1989 | Mouche et al. |
| 4,818,426 A | 4/1989 | Humphreys et al. |
| 4,830,773 A | 5/1989 | Olson |
| 4,834,900 A | 5/1989 | Soldanski et al. |
| 4,849,237 A | 7/1989 | Hurst |
| 4,852,216 A | 8/1989 | Clayton et al. |
| 4,865,752 A | 9/1989 | Jacobs |
| 4,865,855 A | 9/1989 | Hansen et al. |
| 4,900,721 A | 2/1990 | Bansemir et al. |
| 4,906,617 A | 3/1990 | Jacquet et al. |
| 4,908,306 A | 3/1990 | Lorincz |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |
| 4,945,110 A | 7/1990 | Brokken et al. |
| 4,996,062 A | 2/1991 | Lehtonen et al. |
| 4,997,571 A | 3/1991 | Roensch et al. |
| 4,997,625 A | 3/1991 | Simon et al. |
| 4,999,202 A | 3/1991 | Cronje et al. |
| 5,004,760 A | 4/1991 | Patton et al. |
| 5,010,109 A | 4/1991 | Inoi |
| 5,015,408 A | 5/1991 | Reuss |
| 5,030,380 A | 7/1991 | Moschner et al. |
| 5,043,176 A | 8/1991 | Bycroft et al. |
| 5,069,286 A | 12/1991 | Roensch et al. |
| 5,078,896 A | 1/1992 | Rorig et al. |
| 5,084,239 A | 1/1992 | Moulton et al. |
| 5,093,140 A | 3/1992 | Watanabe |
| 5,114,178 A | 5/1992 | Baxter |
| 5,114,718 A | 5/1992 | Damani |
| 5,122,538 A | 6/1992 | Lokkesmoe et al. |
| 5,129,824 A | 7/1992 | Keller |
| 5,130,124 A | 7/1992 | Merianos et al. |
| 5,137,943 A | 8/1992 | Mark |
| 5,139,788 A | 8/1992 | Schmidt |
| 5,143,641 A | 9/1992 | Nunn |
| 5,143,739 A | 9/1992 | Bender et al. |
| 5,168,655 A | 12/1992 | Davidson et al. |
| 5,174,914 A | 12/1992 | Gutzmann |
| 5,176,899 A | 1/1993 | Montgomery |
| 5,178,890 A | 1/1993 | van den Nieuwelaar et al. |
| 5,184,471 A | 2/1993 | Losacco et al. |
| 5,194,163 A | 3/1993 | Saugier |
| 5,200,189 A | 4/1993 | Oakes et al. |
| 5,203,366 A | 4/1993 | Czeck et al. |
| 5,208,057 A | 5/1993 | Greenley et al. |
| 5,220,052 A | 6/1993 | Troughton et al. |
| 5,234,703 A | 8/1993 | Guthery |
| 5,234,719 A | 8/1993 | Richter et al. |
| 5,262,018 A | 11/1993 | Meadow et al. |
| 5,264,229 A | 11/1993 | Mannig et al. |
| 5,266,587 A | 11/1993 | Sankey et al. |
| 5,268,003 A | 12/1993 | Coope et al. |
| 5,292,447 A | 3/1994 | Venturello et al. |
| 5,306,350 A | 4/1994 | Hoy et al. |
| 5,314,687 A | 5/1994 | Oakes et al. |
| 5,320,805 A | 6/1994 | Kramer et al. |
| 5,326,904 A | 7/1994 | Sankey |
| 5,336,500 A | 8/1994 | Richter et al. |
| 5,350,563 A | 9/1994 | Kralovic et al. |
| 5,352,376 A | 10/1994 | Gutzmann |
| 5,364,650 A | 11/1994 | Guthery |
| 5,368,867 A | 11/1994 | Da Silva et al. |
| 5,391,324 A | 2/1995 | Reinhardt et al. |
| 5,393,781 A | 2/1995 | Vegega et al. |
| 5,409,713 A | 4/1995 | Lokkesmoe et al. |
| 5,419,908 A | 5/1995 | Richter et al. |
| 5,435,808 A | 7/1995 | Holzhauer et al. |
| 5,436,008 A | 7/1995 | Richter et al. |
| 5,437,868 A | 8/1995 | Oakes et al. |
| 5,462,681 A | 10/1995 | Gutzmann et al. |
| 5,484,332 A | 1/1996 | Leech et al. |
| 5,489,434 A | 2/1996 | Oakes et al. |
| 5,489,706 A | 2/1996 | Revell |
| 5,494,503 A | 2/1996 | Ross et al. |
| 5,494,588 A | 2/1996 | LaZonby |
| 5,505,740 A | 4/1996 | Kong et al. |
| 5,508,046 A | 4/1996 | Cosentino et al. |
| 5,512,309 A | 4/1996 | Bender et al. |
| 5,527,898 A | 6/1996 | Bauer et al. |
| 5,545,343 A | 8/1996 | Brougham et al. |
| 5,545,374 A | 8/1996 | French et al. |
| 5,550,157 A | 8/1996 | Vegega et al. |
| 5,559,087 A | 9/1996 | Halsrud et al. |
| 5,567,444 A | 10/1996 | Hei et al. |
| 5,578,134 A | 11/1996 | Lentsch et al. |
| 5,591,706 A | 1/1997 | Ploumen |
| 5,595,967 A | 1/1997 | Miracle et al. |
| 5,597,790 A | 1/1997 | Thoen |
| 5,597,793 A | 1/1997 | Besse et al. |
| 5,616,335 A | 4/1997 | Nicolle et al. |
| 5,616,616 A | 4/1997 | Hall et al. |
| 5,624,634 A | 4/1997 | Brougham et al. |
| 5,632,676 A | 5/1997 | Kurschner et al. |
| 5,635,231 A | 6/1997 | Bender et al. |
| 5,641,530 A | 6/1997 | Chen |
| 5,656,302 A | 8/1997 | Cosentino et al. |
| 5,658,467 A | 8/1997 | LaZonby et al. |
| 5,658,595 A | 8/1997 | Van Os |
| 5,674,538 A | 10/1997 | Lokkesmoe et al. |
| 5,674,828 A | 10/1997 | Knowlton et al. |
| 5,683,724 A | 11/1997 | Hei et al. |
| 5,692,392 A | 12/1997 | Swier |
| 5,712,239 A | 1/1998 | Knowlton et al. |
| 5,718,910 A | 2/1998 | Oakes et al. |
| 5,720,983 A | 2/1998 | Malone |
| 5,756,139 A | 5/1998 | Harvey et al. |
| 5,785,867 A | 7/1998 | LaZonby et al. |
| 5,840,343 A | 11/1998 | Hall et al. |
| 5,851,483 A | 12/1998 | Nicolle et al. |

(56) References Cited

U.S. PATENT DOCUMENTS

| | | |
|---|---|---|
| 5,858,117 A | 1/1999 | Oakes et al. |
| 5,858,941 A | 1/1999 | Oakes et al. |
| 5,863,244 A | 1/1999 | Mansfield et al. |
| 5,863,874 A | 1/1999 | Person Hei et al. |
| 5,866,005 A | 2/1999 | DeSimone et al. |
| 5,882,253 A | 3/1999 | Mostoller |
| 5,891,392 A | 4/1999 | Monticello et al. |
| 5,900,256 A | 5/1999 | Scoville, Jr. et al. |
| 5,902,619 A | 5/1999 | Rubow et al. |
| 5,968,539 A | 10/1999 | Beerse et al. |
| 5,977,403 A | 11/1999 | Byers |
| 5,989,611 A | 11/1999 | Stemmler, Jr. et al. |
| 5,998,358 A | 12/1999 | Herdt et al. |
| 6,008,405 A | 12/1999 | Gray et al. |
| 6,010,729 A | 1/2000 | Gutzmann et al. |
| 6,015,536 A | 1/2000 | Lokkesmoe et al. |
| 6,024,986 A | 2/2000 | Hei |
| 6,028,104 A | 2/2000 | Schmidt et al. |
| 6,033,705 A | 3/2000 | Isaacs |
| 6,039,992 A | 3/2000 | Compadre et al. |
| 6,049,002 A | 4/2000 | Mattila et al. |
| 6,080,712 A | 6/2000 | Revell et al. |
| 6,096,226 A | 8/2000 | Fuchs et al. |
| 6,096,266 A | 8/2000 | Duroselle |
| 6,096,348 A | 8/2000 | Miner et al. |
| 6,103,286 A | 8/2000 | Gutzmann et al. |
| 6,111,963 A | 8/2000 | Thompson, III |
| 6,113,963 A | 9/2000 | Gutzmann et al. |
| 6,165,483 A | 12/2000 | Hei et al. |
| 6,183,708 B1 | 2/2001 | Hei et al. |
| 6,183,807 B1 | 2/2001 | Gutzmann et al. |
| 6,238,685 B1 | 5/2001 | Hei et al. |
| 6,245,729 B1 | 6/2001 | Wei et al. |
| 6,257,253 B1 | 7/2001 | Lentsch et al. |
| 6,268,324 B1 | 7/2001 | Besse et al. |
| 6,274,542 B1 | 8/2001 | Carr et al. |
| 6,277,344 B1 | 8/2001 | Hei et al. |
| 6,302,968 B1 | 10/2001 | Baum et al. |
| 6,319,888 B2 | 11/2001 | Wei et al. |
| 6,326,032 B1 | 12/2001 | Richter et al. |
| 6,382,136 B1 | 5/2002 | Bragulla et al. |
| 6,384,006 B1 | 5/2002 | Wei et al. |
| 6,395,703 B2 | 5/2002 | Scepanski |
| 6,423,868 B1 | 7/2002 | Carr et al. |
| 6,451,746 B1 | 9/2002 | Moore et al. |
| 6,455,086 B1 | 9/2002 | Trinh et al. |
| 6,475,961 B2 | 11/2002 | Lokkesmoe et al. |
| 6,479,454 B1 | 11/2002 | Smith et al. |
| 6,489,281 B1 | 12/2002 | Smith et al. |
| 6,506,737 B1 | 1/2003 | Hei et al. |
| 6,514,556 B2* | 2/2003 | Hilgren .............. A01N 37/16 426/321 |
| 6,534,075 B1 | 3/2003 | Hei et al. |
| 6,545,047 B2* | 4/2003 | Gutzmann .......... A01N 37/16 514/557 |
| 6,589,565 B1 | 7/2003 | Richter et al. |
| 6,593,283 B2 | 7/2003 | Hei et al. |
| 6,627,593 B2 | 9/2003 | Hei et al. |
| 6,627,657 B1 | 9/2003 | Hilgren et al. |
| 6,630,434 B2 | 10/2003 | Besse et al. |
| 6,630,439 B1 | 10/2003 | Norwood et al. |
| 6,635,286 B2 | 10/2003 | Hei et al. |
| 6,638,902 B2 | 10/2003 | Tarara et al. |
| 6,674,538 B2 | 1/2004 | Takahashi |
| 6,683,040 B2 | 1/2004 | Bragulla et al. |
| 6,900,167 B2 | 5/2005 | Griese et al. |
| 6,903,062 B2 | 6/2005 | Griese et al. |
| 6,927,237 B2 | 8/2005 | Hei et al. |
| 6,949,178 B2 | 9/2005 | Tennakoon et al. |
| 6,953,507 B2 | 10/2005 | Kravitz et al. |
| 6,962,714 B2 | 11/2005 | Hei et al. |
| 6,964,787 B2 | 11/2005 | Swart et al. |
| 6,991,685 B2 | 1/2006 | Kravitz et al. |
| 6,998,369 B2 | 2/2006 | Hei et al. |
| 7,012,154 B2 | 3/2006 | Vineyard et al. |
| 7,056,536 B2 | 6/2006 | Richter et al. |
| 7,150,884 B1 | 12/2006 | Hilgren et al. |
| 7,316,824 B2 | 1/2008 | Hilgren et al. |
| 7,507,429 B2 | 3/2009 | Man et al. |
| 7,832,360 B2* | 11/2010 | Hilgren .............. A01N 37/16 119/651 |
| 8,030,351 B2 | 10/2011 | Gutzmann et al. |
| 8,043,650 B2* | 10/2011 | Gutzmann .......... A01N 37/16 426/652 |
| 9,560,874 B2* | 2/2017 | Gutzmann .......... A01N 37/16 |
| 9,560,875 B2* | 2/2017 | Gutzmann .......... A01N 37/16 |
| 2002/0128312 A1 | 9/2002 | Hei et al. |
| 2002/0168422 A1 | 11/2002 | Hei et al. |
| 2002/0173545 A1 | 11/2002 | Gutzmann et al. |
| 2003/0070691 A1 | 4/2003 | Giletto et al. |
| 2003/0087786 A1 | 5/2003 | Hei et al. |
| 2003/0199583 A1 | 10/2003 | Gutzmann et al. |
| 2005/0152991 A1 | 7/2005 | Man et al. |
| 2005/0192197 A1 | 9/2005 | Man et al. |
| 2007/0292580 A1 | 12/2007 | Gutzmann et al. |

FOREIGN PATENT DOCUMENTS

| | | |
|---|---|---|
| DK | 9300538 | 11/1994 |
| EP | 0 017 681 | 5/1983 |
| EP | 0 167 375 | 1/1986 |
| EP | 0 186 052 | 7/1986 |
| EP | 0 195 619 | 9/1986 |
| EP | 0 125 781 | 8/1987 |
| EP | 0 233 731 | 8/1987 |
| EP | 0 242 990 | 10/1987 |
| EP | 0 105 689 | 12/1987 |
| EP | 0 140 648 | 3/1989 |
| EP | 0 168 587 | 7/1989 |
| EP | 0 361 955 | 4/1990 |
| EP | 0 404 293 | 12/1990 |
| EP | 0 461 700 | 12/1991 |
| EP | 0 569 066 | 11/1993 |
| EP | 0 667 392 | 8/1995 |
| EP | 0 460 962 | 12/1995 |
| EP | 0 540 515 | 12/1995 |
| EP | 0 779 357 | 6/1997 |
| EP | 0 603 329 | 8/1997 |
| EP | 0 805 198 | 11/1997 |
| EP | 0 843 001 | 5/1998 |
| EP | 0 967 203 | 12/1999 |
| EP | 0 985 349 | 3/2000 |
| EP | 0 946 506 | 9/2003 |
| EP | 1 382 666 | 1/2004 |
| EP | 1 435 203 | 7/2004 |
| EP | 1 307 099 | 10/2005 |
| FR | 2 321 301 | 3/1977 |
| FR | 2 324 626 | 4/1977 |
| FR | 2 578 988 | 9/1986 |
| GB | 947688 | 1/1964 |
| GB | 1494109 | 12/1977 |
| GB | 2020257 | 11/1979 |
| GB | 1570492 | 7/1980 |
| GB | 2182051 | 5/1987 |
| GB | 2187958 | 9/1987 |
| GB | 2207354 | 2/1989 |
| GB | 2255507 | 11/1992 |
| GB | 2257630 | 1/1993 |
| GB | 2353800 | 3/2001 |
| JP | 7-31210 | 2/1995 |
| JP | 7-258005 | 10/1995 |
| JP | 11-349560 | 12/1999 |
| JP | 2000060418 | 2/2000 |
| JP | 2000290251 | 10/2000 |
| LU | 78 568 | 4/1978 |
| NL | 9201631 | 9/1992 |
| NZ | 0337244 | 12/2000 |
| RU | 2102447 | 1/1998 |
| SU | 1172514 | 8/1985 |
| SU | 1750677 | 7/1992 |
| UA | 71 893 | 2/2001 |
| WO | WO-91/07375 | 5/1991 |
| WO | WO-93/01716 | 2/1993 |
| WO | WO-94/06294 | 3/1994 |

(56) References Cited

FOREIGN PATENT DOCUMENTS

| | | |
|---|---|---|
| WO | WO-94/14321 | 7/1994 |
| WO | WO-94/15465 | 7/1994 |
| WO | WO-94/21122 | 9/1994 |
| WO | WO-94/23575 | 10/1994 |
| WO | WO-95/28472 | 10/1995 |
| WO | WO-95/34537 | 12/1995 |
| WO | WO-96/30474 | 10/1996 |
| WO | WO-98/04143 | 2/1998 |
| WO | WO-98/28267 | 7/1998 |
| WO | WO-99/51095 | 10/1999 |
| WO | WO-00/18870 | 4/2000 |
| WO | WO-01/47359 | 7/2001 |
| WO | WO-02/03799 | 1/2002 |
| WO | WO-02/054866 | 7/2002 |
| WO | WO-02/060280 | 8/2002 |
| WO | WO-2004/043162 | 5/2004 |

OTHER PUBLICATIONS

Baldry, Journal of Applied Bacteriology (1983) 54:417-423.
Bayliss et al., FEMS Microbiology Letters (1979) 5:331-333.
Bell et al., Food Microbiology (1997) 14:439-448.
Beuchat, Dairy, Food and Environmental Sanitation (1992) 12:6-9.
Block, "Peroxygen Compounds," Disinfection, Sterilization, and Preservation, Fourth Ed., Chapter 9, pp. 167-181 (1991).
Block, "Peroxygen Compounds," Disinfection, Sterilization, and Preservation, Fifth Ed., Chapter 9, pp. 185-204 (2001).
Breen et al., Journal of Food Protection (1997) 60(9):1019-1021.
Breen et al., Journal of Food Science (1995) 60(6):1191-1196.
Brown, Plant Disease (1987) 319-323.
Buck, Infection Control Today (2001), available online at http://www.infectioncontroltoday.com/articles/19clean.html#.
Chance, Journal of Biological Chemistry (1949) 179:1341-1369.
Computer search results—Level 1-5 patents (Mar. 2004).
Computer search results from Ecolab Information Center (Jun. 1988).
Cords, "New Peroxyacetic Acid Sanitizer", Proceedings, Twenty-Third Convention, Institute of Brewing, Sydney, Australia, (1994) pp. 165-169.
Crozier-Dodson et al., Food Safety Magazine (2004), "Formulating Food Safety: An Overview of Antimicrobial Ingredients", available at www.foodsafetymagazine.com.
Degussa Corporation, Premarket Approval Request to the Food and Drug Administration (FDA), dated Apr. 28, 1994.
Dickens et al., Poultry Science (1997) 76:657-660.
Dickens et al., Poultry Science (1994) 73:582-586.
Dickens et al., Poultry Science (1994) 73:576-581.
Dickens et al., Poultry Science (1995) 74:1044-1048.
Dickson et al., Journal of Food Protection (1992) 55(2):133-140.
Dorn et al., Arch. Fur Geflugelkunde (1989) 53(3):123-134.
Eggensperger, Zbl. Bakt. Hyg., I. Abt. Orig. B (1979) 168:517-524.
Emery Industries, "Emery Fatty and Dibasic Acids Specifications and Characteristics", Bulletin 145 (Oct. 1983).
Fatemi et al., Journal of Food Protection (1999) 62(7):761-765 (abstract only).
Federal Register, 61:15024-15027, USDA-FSIS. Washington DC, (1996), "Notice of Policy Change; Achieving the Zero Tolerance Performance Standard for Beef Carcasses by Knife Trimming and Vacuuming With Hot Water or Steam; Use of Acceptable Carcass Interventions for Reducing Carcass Contamination Without Prior Agency Approval."
Federal Register, vol. 68, #28, Tuesday Feb. 11, 2003 at 6875.
Federal Register, vol. 61, #144, Thursday Jul. 25, 1996 at 38940.
Focus on Interox, Effluent & Water Treatment Journal, 4 pages (Aug. 1979).
Food and Drug Administration (1982), "Gras status of acetic acid, ammonium acetate, sodium acetate, and sodium diacetate", Federal Register 47:27813-27814.
Fraser, Specialty Chemicals (1987) 7(3):178-186.
Greenspan et al., Food Technology (1951) 5(3):95-97.
Gusev et al., Veterinary Disease Control Review (1998) Feb:44-46.
Han et al., Journal of Food Processing and Preservation (1980) 4:95-110.
Heinemann, JAMA (1913) LX(21):1603-1606.
Higgins, Food Engineering (2002), available online at www.foodengineeringmag.com.
Hilgren et al., U.S. Appl. No. 09/614,631, filed Jul. 12, 2000.
Hutchings et al., "Comparative Evaluation of the Bactericidal Efficiency of Peracetic Acid, Quaternaries, and Chlorine Containing Compounds," Presented at the 49$^{th}$ General Meeting of the Society of American Bacteriologists, (Abstract), pp. 50-51 (May 17-20, 1949).
International Search Report for PCT/US01/51073, dated Jun. 3, 2002, 8 pages.
International Search Report for PCT/US01/20209, dated Jan. 30, 2002, 9 pages.
International Search Report for PCT/US02/21777, dated Dec. 27, 2002, 4 pages.
International Search Report for PCT/US2005/000147, dated Jul. 4, 2005, 7 pages.
International Search Report for PCT/US2005/000149, dated Jun. 28, 2005, 7 pages.
International Search Report for PCT/US2005/000151, dated May 3, 2005, 8 pages.
International Search Report for PCT/US2005/000231, dated Jun. 28, 2005, 5 pages.
Interox Chemicals Ltd. product brochure entitled: Oxymaster Peracetic Acid 12%.
Interox Chemicals Ltd. product brochure entitled: Proxitane 4002 Peracetic Acid 36-40%.
Jager et al., Mitt. Versuch. Gaorung. Wien. (1980) 34:32-36.
Kim et al., Journal of Food Protection (1995) 59(3):322-326.
Kim et al., Poultry Science (2005) 84(11):1778-84.
Kunzmann, Fortschr. Med. (1934) 52(16):357-359.
Krushinskie, "*Salmonella* Interventions in the U.S. Broiler Industry" presented at the USDA's Food Safety and Inspection Service meting "Advances in Post-Harvest Interventions to Reduce *Salmonella* in Poultry" on Feb. 23-24, 2006. Available at http://www.fsis.usda.gov/News_&_Events/Presentations_PostHarvest_022306/index.asp.
Laska et al., Am. J. Physiol. (1998) 274:R1639-R1645.
Lillard and Thomson, Journal of Food Science (1983) 48:125-126.
Lillard, Journal of Food Protection (1985) 48(9):803-807.
Lillard, Journal of Food Protection (1989) 52(11):829-832.
Lion et al., Bull. Soc. Chim. Belg. (1991) 100(7):555-559.
Merka et al., Chemical Abstracts (1967) vol. 67, Abstract No. 67542e.
MicroPatent report dated Aug. 18, 2003.
Mulder et al., Poultry Science (1987) 66:1555-1557.
Northcutt et al., Poultry Science (2005) 84:1648-1652.
Nambudripad et al., Indian Journal of Dairy Science (1949) 4:65-69.
Opinion Letter dated Apr. 11, 2000.
Orth et al., Fleischwirtsch (1989) 69(10):1575-1576.
Park et al., Dairy, Food and Environmental Sanitation (1999) 19(12):842-847 (abstract only).
Parker et al., Synthesis and Properties of Long Chain Aliphatic Peracids (1955) 77:4037-4041.
Parker et al., Aliphatic Diperacids (1957) 79:1929-1931.
Pfizer Chemical Division, "Pfizer Flocon Biopolymers for Industrial Uses (xanthan broths)", Data Sheet 679, pp. 1-4 (year unknown).
Poffe et al., Zbl. Bakt. Hyg. I. Abt. Orig. B (1978) 167:337-346.
"PerSafe Direct Meat Intervention" available at www.afcocare.com.
Press release "Ecolab Closes on Purchase of Alcide", dated Jul. 30, 2004. Available at www.ecolab.com.
Press release "New Food Safety Technology Approved by FDA", dated Jan. 22, 2001. Available at www.ecolab.com.
Press release "FDA Approves Alcide Food Additive Petition of use of SANOVA on Red Meat", dated Mar. 6, 1998. Available at http://www.spcnetwork.com/mii/1998/980309.htm.
Quaas and Kruger, Fleisch (1980) 34(4):73-75.
Ranganna et al., Indian Food Packer (1981) 30-45.

(56) References Cited

OTHER PUBLICATIONS

Reynolds, "Utilization of spray wash with organic aids (peroxyactic acid and lactic acid) and chlorinated wash in combination, utilizing direct application methods, for pathogen reduction on pork and beef carcasses in small and very small meat processing plants", available as C-29 at www.fsis.usda.gov.
Richardson, The Lancet (1891) 707-709, 760-763.
Russian Federation Ministry of Agriculture, "Measures to lower the microbe contamination of poultry, egg shells, poultry meat products and eggs and their *Salmonella* decontamination," (1994) pp. 1-14.
Search Report for the use of amine oxides with hydrogen peroxide in bleaching, sanitizing, disinfectant or hard surface cleaners.
Search results from Database WPI and Database INPADOC.
Search Results (2003).
Sims, Chemistry and Industry (1983) 14:555-558.
Solvay product brochure entitled: Oxymaster—Proxitane Peracetic Acid Applications.
Solvay product brochure entitled: Oxymaster—Proxitane Peracetic Acid Solutions; Handling, Storage and Transport Information (Safety Documentation).
Tamblyn et al., Journal of Food Protection (1997) 60(6):629-633.
Taylor et al., Journal of Applied Microbiology (1999) 87:718-725.
Towle et al., "Industrial Gums Polysaccharides and Their Derivatives" Second Ed., Chapter XIX, pp. 429-444 (year unknown).
Xiong et al., Journal of Food Protection (1998) 61(3):272-275.
Yoshpe et al., Health Laboratory Science (1968) 5(4):233-238.
Application as filed from U.S. Appl. No. 09/137,242, filed Aug. 20, 1998.
Notice of Allowance from U.S. Appl. No. 09/137,242, dated Aug. 6, 1999.
Application as filed from U.S. Appl. No. 09/419,019, filed Oct. 15, 1999.
Notice of Allowance from U.S. Appl. No. 09/419,019, dated Dec. 7, 1999.
Amendment under 37 CFR § 1.312 from U.S. Appl. No. 09/419,019, filed on Dec. 29, 1999.
Application as filed from U.S. Appl. No. 09/368,452, filed Aug. 3, 1999.
Terminal Disclaimer from U.S. Appl. No. 09/368,452, filed on Mar. 16, 2000.
Notice of Allowance from U.S. Appl. No. 09/368,452, dated Mar. 21, 2000.
Application as filed from U.S. Appl. No. 09/591,423, filed Jun. 9, 2000.
Notice of Allowance from U.S. Appl. No. 09/591,423, dated Sep. 7, 2000.
Application as filed from U.S. Appl. No. 09/634,502, filed Aug. 9, 2000.
Non-Final Office Action from U.S. Appl. No. 09/634,502, dated Aug. 28, 2001.
Non-Final Office Action from U.S. Appl. No. 10/084,697, dated May 9, 2002.
Amendment and Response from U.S. Appl. No. 10/084,697, dated Aug. 9, 2002.
Supplemental Amendment from U.S. Appl. No. 10/084,697, dated Aug. 15, 2002.
Notice of Allowance from U.S. Appl. No. 10/084,697, dated Nov. 8, 2002.
Non-Final Office Action from U.S. Appl. No. 10/370,798, dated Oct. 17, 2003.
Amendment and Response from U.S. Appl. No. 10/370,798, filed on Jan. 20, 2004.
Resubmission of Listing of Claims Portion of Amendment and Response filed Jan. 20, 2004 from U.S. Appl. No. 10/370,798, filed on Feb. 17, 2004.
Restriction Requirement from U.S. Appl. No. 10/370,798, dated Jun. 1, 2004.
Amendment and Response from U.S. Appl. No. 10/370,798, filed on Jul. 1, 2004.
Non-Final Office Action from U.S. Appl. No. 10/370,798, dated Oct. 18, 2004.
Non-Final Office Action from U.S. Appl. No. 10/370,798, dated Dec. 7, 2004.
Amendment and Response from U.S. Appl. No. 10/370,798, filed on Mar. 22, 2005.
Notice of Allowance from U.S. Appl. No. 10/370,798, dated Jun. 28, 2005.
Request for Continued Examination from U.S. Appl. No. 10/370,798, filed on Sep. 28, 2005.
Non-Final Office Action from U.S. Appl. No. 10/370,798, dated Dec. 29, 2005.
Response from U.S. Appl. No. 10/370,798, filed on Feb. 2, 2006.
Non-Final Office Action from U.S. Appl. No. 10/370,798, dated Apr. 27, 2006.
Response from U.S. Appl. No. 10/370,798, filed on Aug. 28, 2006.
Restriction Requirement from U.S. Appl. No. 10/370,798, dated Jul. 16, 2007.
Complaint, from *Ecolab, Inc.* v. *FMC Corporation*, filed Apr. 26, 2005 in the United States District Court for the District of Minnesota, Case No. 0:05-cv-00831-JMR-FLN.
Answer to Complaint, Affirmative Defenses, and Counterclaim, filed Aug. 11, 2005.
Plaintiff's Reply to Defendant's Counterclaim, filed Aug. 31, 2005.
First Amended Complaint, filed Oct. 12, 2005.
Answer to First Amended Complaint, Affirmative Defenses, and Counterclaim, filed Oct. 26, 2005.
Stipulation Regarding Joint Claim Construction Statement and Request for Markman Hearing, filed Apr. 21, 2006.
FMC Corporation's Opening Claim Construction Brief, filed Apr. 21, 2006.
Declaration of Scott M. Russell, Ph.D., filed Apr. 21, 2006.
Declaration of Francis DiGiovanni Submitted in Support of FMC Corporation's Opening Claim Construction Brief, filed Apr. 21, 2006.
Plaintiff Ecolab Inc.'s Opening Claim Construction Brief, filed Apr. 21, 2006.
Declaration of Timothy A. Gutzmann in Support of Ecolab's Opening Claim Construction Brief, filed Apr. 21, 2006.
Declaration of Rachel K. Zimmerman, filed Apr. 21, 2006.
FMC Corporation's Opening Claim Construction Brief (Amended), filed Apr. 26, 2006.
Plaintiff Ecolab Inc.'s Answering Claim Construction Brief, filed May 10, 2006.
Declaration of Martin P. Rigney in Support of Ecolab Inc.'s Answering Claim Construction Brief, filed May 10, 2006.
Declaration of R. Bruce Tompkin, Ph.D. in Support of Ecolab Inc.'s Answering Claim Construction Brief, filed May 10, 2006.
Declaration of Rachel K. Zimmerman in Support of Ecolab Inc.'s Answering Claim Construction Brief, filed May 10, 2006.
FMC Corporation's Answering Claim Construction Brief, filed May 10, 2006.
Second Declaration of Scott M. Russell, Ph.D., filed May 10, 2006.
Declaration of Francis DiGiovanni Submitted in Support of FMC Corporation's Answering Claim Construction Brief, filed May 10, 2006.
Preliminary Claim Construction, filed May 11, 2006.
FMC Corporation's Response to the Court's Preliminary Claim Construction, filed Jun. 1, 2006.
Second Amended Complaint, filed Jun. 9, 2006.
Answer to Second Amended Complaint, Affirmative Defenses, and Counterclaim, filed Jun. 23, 2006.
Plaintiff Ecolab Inc.'s Motion for a Protective Order and for Sanctions, filed Aug. 9, 2006.
Plaintiff Ecolab Inc.'s Memorandum in Support of its Motion for a Protective Order and for Sanctions, filed Aug. 9, 2006.
Declaration of Andrew D. Sorenson, Esq. in Support of Ecolab Inc.'s Motion for a Protective Order and for Sanctions, filed Aug. 9, 2006.
Declaration of Rachel K. Zimmerman in Support of Ecolab Inc.'s Motion for a Protective Order and for Sanctions, filed Aug. 9, 2006.
Declaration of Douglas J. Williams in Support of Ecolab Inc.'s Motion for a Protective Order and for Sanctions, filed Aug. 9, 2006.

(56) References Cited

OTHER PUBLICATIONS

Defendant FMC Corporation's Motion for Sanctions and an Order Allowing FMC to Re-Notice and Take the Deposition of B. Eugene Guthery, filed Aug. 14, 2006.
FMC Corporation's Memorandum in Support of its Motion for Sanctions and an Order Allowing FMC to Re-Notice and Take the Deposition of B. Eugene Guthery, filed Aug. 14, 2006.
Declaration of Francis DiGiovanni, Esq., filed Aug. 14, 2006.
Plaintiff's Reply to Defendant's First Amended Counterclaim, filed Aug. 17, 2006.
Plaintiff Ecolab Inc.'s Memorandum in Opposition to FMC Corporation's Motion for Sanctions and an Order Allowing FMC to Re-Notice and Take the Deposition of B. Eugene Guthery, filed Aug. 21, 2006.
FMC Corporation's Memorandum in Opposition to Plaintiff's Motion for a Protective Order and for Sanctions, filed Aug. 21, 2006.
Declaration of Thomas L. Hamlin in Support of Plaintiff Ecolab's Motion to Strike Untimely Expert Report and Exclude Expert Testimony, filed Oct. 31, 2006.
Order Modifying Claim Construction, filed Nov. 3, 2006.
Affidavit of H. Sanders Gwin, Jr. In Support of Ecolab's Memorandum in Opposition to FMC's Motion to Exclude the Trial Testimony of Ecolab's Patent Law Expert, filed Nov. 20, 2006.
Affidavit of Andrew D. Sorenson, Chief Patent Counsel of Ecolab Inc., in Support of Ecolab's Memorandum in Opposition to FMC's Motion to Exclude the Trial Testimony of Ecolab's Patent Law Expert, filed Nov. 20, 2006.
Ecolab's Motion for Summary Judgment of Non-Infringement, filed Dec. 18, 2006.
FMC Corporation's Motion for Summary Judgment, filed Dec. 18, 2006.
Declaration of R. Bruce Tompkin, Ph.D. in Support of Ecolab's Motion for Summary Judgment, filed Jan. 18, 2007.
Order (Denying Motions for Summary Judgment), filed Mar. 28, 2007.
Ecolab's Motion for a Stay Pending Reexamination, filed Apr. 12, 2007.
Memorandum of Law in Support of Ecolab's Motion for a Stay Pending Reexamination, filed Apr. 12, 2007.
Declaration of Ross Abbey in Support of Ecolab's Motion for a Stay Pending Reexamination, filed Apr. 12, 2007.
Order (Denying Motion for a Stay), filed May 30, 2007.
Joint Statement of Agreed Facts and Joint Exhibit List, filed Jun. 5, 2007.
Plaintiff Ecolab Inc.'s Concise Statement of its Case-in-Chief and Exhibit List, filed Jun. 11, 2007.
FMC Corporation's Concise Statement of its Case-in-Chief and Exhibit List, filed Jun. 11, 2007.
Plaintiff's Supplemental Exhibit List, filed Jun. 28, 2007.
Plaintiff Ecolab Inc.'s Objections to Defendant's Exhibit List, filed Jul. 2, 2007.
Plaintiff Ecolab Inc.'s Motion in Limine No. 1 to Exclude Evidence Regarding the Alleged Inventorship of Dr. Eugene Guthery and "Inequitable Conduct" Evidence and Argument, filed Jul. 2, 2007.
FMC's Memorandum of Law: FMC's Motion in Limine No. 2: to Exclude Evidence Regarding Ecolab's Irrelevant Patents and Regulatory Filings, filed Jul. 2, 2007.
FMC's Objections to Ecolab's Exhibit List, filed Jul. 2, 2007.
Plaintiff Ecolab's Proposed Jury Instructions, filed Jul. 9, 2007.
Plaintiff Ecolab's Proposed Voir Dire Questions, filed Jul. 9, 2007.
Plaintiff Ecolab's Proposed Special Verdict Form, filed Jul. 9, 2007.
FMC Corporation's Proposed Substantive Jury Instructions, filed Jul. 9, 2007.
FMC Corporation's Proposed Voir Dire, filed Jul. 9, 2007.
FMC Corporation's Proposed Special Verdict Form, filed Jul. 9, 2007.
Defendant's Supplemental Exhibit List, filed Jul. 13, 2007.
FMC Corporation's Revised Proposed Substantive Jury Instructions, filed Jul. 17, 2007.

Plaintiff Ecolab Inc.'s Objections to Defendant's Supplemental Exhibit List, filed Jul. 19, 2007.
FMC's Memorandum of Law in Opposition to Ecolab's Motion in Limine No. 1: To Exclude Evidence Regarding the Inventorship of Dr. Eugene Guthery and Inequitable Conduct Evidence and Argument, filed Jul. 25, 2007.
FMC's Memorandum of Law in Opposition to Ecolab's Motion in Limine No. 2: to Exclude All References to or Evidence of the Pending Reexaminations of the Patents-in-Suit, filed Jul. 25, 2007.
FMC's Memorandum of Law in Opposition to Ecolab's Motion in Limine No. 3: To Exclude the Expert Opinion Testimony and Experiments of Dr. Scott Russell, filed Jul. 25, 2007.
Plaintiff's Second Supplemental Exhibit List, filed Aug. 31, 2007.
Defendant's Second Supplemental Exhibit List, filed Sep. 5, 2007.
Plaintiff Ecolab Inc.'s Answers to FMC's First Set of Interrogatories (Nos. 1-16), filed Oct. 11, 2005.
Plaintiff Ecolab Inc.'s Supplemental Answers to FMC's First Set of Interrogatories (No. 16), filed Mar. 10, 2006.
Plaintiff Ecolab Inc.'s Supplemental Answer to FMC's Interrogatory No. 2 and Second Supplemental Answer to FMC's Interrogatory No. 14, filed Apr. 3, 2006.
FMC Corporation's Responses and Objections to Ecolab Inc.'s First Set of Interrogatories (1-12), filed Oct. 17, 2005.
FMC Corporation's Supplemental Responses and Objections to Ecolab Inc.'s Interrogatories 1 and 2, filed Nov. 30, 2005.
FMC Corporation's Supplemental and Amended Responses and Objections to Ecolab Inc.'s Interrogatories, filed Mar. 1, 2006.
FMC Corporation's Responses and Objections to Ecolab Inc.'s Second Set of Interrogatories (13-23), filed Jul. 11, 2006.
FMC Corporation's Jul. 31, 2006 Supplemental and Amended Responses and Objections to Ecolab Inc.'s First Set of Interrogatories, filed Jul. 31, 2006.
FMC Corporation's Supplemented and Amended Responses and Objections to Ecolab Inc.'s Second Set of Interrogatories (13-23), filed Jul. 31, 2006.
FMC Corporation's "Prior Art Statement", filed Mar. 17, 2006.
Ecolab's Prior Art Statement, filed Mar. 17, 2006.
Ecolab's Response to FMC's Prior Art Statement, filed Apr. 3, 2006.
FMC Corporation's Response to Ecolab's Prior Art Statement, filed Apr. 3, 2006.
FMC Corporation's Amended and Supplemented "Prior Art Statement", filed Jul. 31, 2006.
FMC Corporation's Responses and Objections to Ecolab Inc.'s First Set of Requests for Admission (1-37), filed Nov. 14, 2005.
Ecolab's Responses to FMC's First Set of Requests for Admissions (Nos. 1-67), filed Jul. 11, 2006.
Plaintiff Ecolab Inc.'s Preliminary Proposed Claim Construction Statement, filed Mar. 25, 2006.
Plaintiff Ecolab Inc.'s Amended Preliminary Proposed Claim Construction Statement, filed Apr. 4, 2006.
Plaintiff Ecolab Inc.'s Preliminary Designation of Claim Terms for Construction, filed Mar. 1, 2006.
FMC's Chart of Claim Terms Needing Construction, filed Mar. 1, 2006.
Court Docket from PACER for *Ecolab, Inc. v. FMC Corporation*, U.S. District Court for the District of Minnesota, Case No. 0:05-CV-00831-JMR-FLN, accessed Sep. 6, 2007.
Request for Reexamination of U.S. Pat. No. 6,010,729, filed Apr. 12, 2007.
Order Granting Request for Reexamination of U.S. Pat. No. 6,010,729, Control No. 90/008,592, dated Jul. 11, 2007.
Request for Reexamination of U.S. Pat. No. 6,103,286, filed Apr. 12, 2007.
Order Granting Request for Reexamination of U.S. Pat. No. 6,103,286, Control No. 90/008,587, dated Jul. 11, 2007.
Request for Reexamination of U.S. Pat. No. 6,113,963, filed Apr. 12, 2007.
Order Granting Request for Reexamination of U.S. Pat. No. 6,113,963, Control No. 90/008,593, dated Jul. 10, 2007.
Request for Reexamination of U.S. Pat. No. 5,632,676, filed Apr. 12, 2007.
Order Granting Request for Reexamination of U.S. Pat. No. 5,632,676, Control No. 90/008,588, dated Jun. 1, 2007.

(56) References Cited

OTHER PUBLICATIONS

Bolder, Trends in Food Science & Technology (1997) 8:221-227.
Cutter & Si Ragusa, Food Microbiology (1994) 11:481-489.
Cutter & Si Ragusa, Journal of Food Protection (1994) 57(2):97-103.
Dickson et al., Journal of Food Protection (1994) 57(11):952-955.
Dorsa et al., Journal of Food Protection (1996) 59(2):127-135.
Dorsa et al., Journal of Food Protection (1997) 60(2):114-119.
Dorsa et al., Journal of Food Protection (1997) 60(6):619-624.
Evans, Wiley Encyclopedia of Food Science and Tech. (2000) 1:501-509.
Farber & Idziak, Journal of Food Protection (1984) 47(2):92-95.
Firstenberg-Eden, Journal of Food Protection (1981) 44(8):602-607.
Izat et al., Journal of Food Protection (1989) 52(9):670-673.
Kochevar et al., Meat Science (1997) 45(3):377-388.
Labadie et al., European Journal of Applied Microbiology (1977) 4:67-73.
Mosteller & Bishop, Journal of Food Protection (1993) 56(1):34-41.
Pan et al., J. Agric. Food Chem. (1999) 47:3325-3331.
Sagripanti et al., Am. J. Infect. Control (1997) 22:335-339.
Snijders et al., The Veterinary Quarterly (1985) 7(4):277-282.
Alexy et al., The American Midland Naturalist (2003) 149(1):237-240.
Davies & Deary, Journal of Chemical Research, Synopses (1988) 11:354-355.
Stier, Meat and Poultry (2000) 10:46-51.
Kotula et al., Journal of Animal Science (1974) 39(4):674-679.
FMC's Motion to Preclude Ecolab from Presenting "Indefiniteness" Arguments and Evidence to the Jury, filed Sep. 17, 2007.
FMC's Memorandum of Law in Support of Its Motion to Preclude Ecolab from Presenting "Indefiniteness" Arguments and Evidence to the Jury, filed Sep. 17, 2007.
Declaration of Francis DiGiovanni, Esq., filed Sep. 17, 2007.
Plaintiff's Third Supplemental Exhibit List, filed Sep. 18, 2007.
Plaintiff Ecolab Inc.'s Objections to Defendant's Second Supplemental Exhibit List, filed Sep. 18, 2007.
Defendant's Third Supplemental Exhibit List, filed Sep. 18, 2007.
Plaintiff Ecolab Inc.'s Amended Proposed Jury Instructions, filed Sep. 19, 2007.
Plaintiff Ecolab Inc.'s Amended Proposed Special Verdict Form, filed Sep. 19, 2007.
FMC Corporation's Proposed Preliminary Jury Instructions, filed Sep. 21, 2007.
Plaintiff Ecolab Inc.'s Objections to Defendant's Third Supplemental Exhibit List, filed Sep. 22, 2007.
Plaintiff's Fourth Supplemental Exhibit List, filed Sep. 22, 2007.
Plaintiff's Consolidated Exhibit List, filed Sep. 22, 2007.
Defendant FMC Corporation's Objections to Plaintiff's Supplemental Exhibit Lists, filed Sep. 22, 2007.
Defendant's Fourth Supplemental Exhibit List, filed Sep. 23, 2007.
Defendant's Fifth Supplemental Exhibit List, filed Sep. 27, 2007.
FMC Corporation's Proposed Supplemental and Amended Jury Instructions, filed Sep. 27, 2007.
Plaintiff Ecolab Inc.'s Second Amended Proposed Jury Instructions, filed Sep. 30, 2007.
FMC Corporation's Second Supplemental Proposed Jury Instructions, filed Oct. 3, 2007.
Defendant's Sixth Supplemental Exhibit List, filed Oct. 5, 2007.
Plaintiff Ecolab Inc.'s Objections to Defendants Fourth, Fifth and Sixth Supplemental Exhibit Lists, filed Oct. 8, 2007.
Plaintiff's Motion in Limine to Exclude Expert Testimony, filed Oct. 9, 2007.
Memorandum of Law in Support of Plaintiff's Motion in Limine to Exclude Expert Testimony, filed Oct. 9, 2007.
Declaration of Ross Abbey in Support of Memorandum of Law in Support of Plaintiff's Motion in Limine to Exclude Expert Testimony, filed Oct. 9, 2007.
Corrected Memorandum of Law in Support of Plaintiff's Motion in Limine to Exclude Expert Testimony, filed Oct. 9, 2007.
Defendant's Seventh Supplemental Exhibit List, filed Oct. 9, 2007.
Plaintiff Ecolab Inc.'s Objections to Defendant's Seventh Supplemental Exhibit List, filed Oct. 9, 2007.
Defendant's Eighth Supplemental Exhibit List, filed Oct. 10, 2007.
Supplemental Memorandum of Law in Support of Plaintiff's Motion in Limine to Exclude Expert Testimony, filed Oct. 17, 2007.
Plaintiff Ecolab Inc.'s Proposed Additional Jury Instructions, filed Oct. 18, 2007.
Plaintiff's Fifth Supplemental Exhibit List, filed Oct. 20, 2007.
Jury Special Verdict, entered Nov. 7, 2007.
Order (on jury verdict directing entry of judgment), entered Nov. 8, 2007.
Judgment in a Civil Case, entered Nov. 8, 2007.
Ecolab's Motion for a Permanent Injunction Prohibiting Infringement of U.S. Pat. Nos. 6,010,729 and 6,113,963, filed Nov. 21, 2007.
Memorandum of Law in Support of Ecolab's Motion for a Permanent Injunction Prohibiting Infringement of U.S. Pat. Nos. 6,010,729 and 6,113,963, filed Nov. 21, 2007.
FMC's Renewed Motion for Judgment as a Matter of Law, or in the Alternative a New Trial, of Obviousness of Claim 7 of Ecolab's 729 Patent, filed Nov. 27, 2007.
FMC's Memorandum of Law in Support of Its Renewed Motion for Judgment as a Matter of Law, or in the Alternative a New Trial, of Obviousness of Claim 7 of Ecolab's '729 Patent, filed Nov. 27, 2007.
FMC's Renewed Motion for Judgment as a Matter of Law, or in the Alternative a New Trial, of Obviousness of Claims 25-28 of Ecolab's '963 Patent, filed Nov. 27, 2007.
FMC's Memorandum of Law in Support of Its Renewed Motion for Judgment as a Matter of Law, or in the Alternative a New Trial, of Obviousness of Claims 25-28 of Ecolab's '963 Patent, filed Nov. 27, 2007.
FMC's Renewed Motion for Judgment as a Matter of Law, or in the Alternative a New Trial, of Anticipation of Claims 17 and 22 of Ecolab's '963 Patent, filed Nov. 27, 2007.
FMC's Memorandum of Law in Support of Its Renewed Motion for Judgment as a Matter of Law, or in the Alternative a New Trial, of Anticipation of Claims 17 and 22 of Ecolab's '963 Patent, filed Nov. 27, 2007.
FMC's Renewed Motion for Judgment as a Matter of Law of No Willful Infringement of Ecolab's Patents, filed Nov. 27, 2007.
FMC's Memorandum of Law in Support of Its Renewed Motion for Judgment as a Matter of Law of No Willful Infringement of Ecolab's Patents, filed Nov. 27, 2007.
FMC's Renewed Motion for Judgment as a Matter of Law, or in the Alternative a New Trial, of Anticipation of Claim 7 of Ecolab's '729 and '963 Patents, filed Nov. 27, 2007.
FMC's Memorandum of Law in Support of Its Renewed Motion for Judgment as a Matter of Law, or in the Alternative a New Trial, of Anticipation of Claim 7 of Ecolab's '729 and '963 Patents, filed Nov. 27, 2007.
Ecolab's Renewed Motion for Judgment as a Matter of Law, filed Nov. 27, 2007.
Ecolab's Memorandum of Law in Support of Its Renewed Motion for Judgment as a Matter of Law, filed Nov. 27, 2007.
Declaration of Ross Abbey in Support of Ecolab's Renewed Motion for Judgment as a Matter of Law, filed Nov. 27, 2007.
Declaration of Francis DiGiovanni Submitted in Support of FMC Corporation's Memorandums of Law in Support of Its Renewed Motions for Judgment as a Matter of Law, filed Nov. 27, 2007.
FMC's Motion for Prejudgment Interest, Accounting of Infringing Activity, and a Permanent Injunction, filed Nov. 27, 2007.
FMC's Memorandum of Law in Support of Its Motion for Prejudgment Interest, Accounting of Infringing Activity, and a Permanent Injunction, filed Nov. 27, 2007.
Court Docket from PACER for *Ecolab, Inc.* v. *FMC Corporation*, U.S. District Court for the District of Minnesota, Case No. 0:05-cv-00831-JMR-FLN, accessed Nov. 30, 2007.
U.S. Appl. No. 08/134,995, filed by Kurschner et al. Oct. 12, 1993.
Non-Final Office Action from U.S. Appl. No. 08/134,995, dated Jun. 9, 1994.
Amendment from U.S. Appl. No. 08/134,995, filed Oct. 6, 1994.

(56) References Cited

OTHER PUBLICATIONS

Final Office Action from U.S. Appl. No. 08/134,995, dated Mar. 3, 1995.
Amendment from U.S. Appl. No. 08/134,995, filed on Aug. 30, 1995.
Non-Final Office Action from U.S. Appl. No. 08/134,995, dated Jan. 5, 1996.
Amendment from U.S. Appl. No. 08/134,995, filed on Jul. 3, 1996.
Notice of Allowance from U.S. Appl. No. 08/134,995, dated Oct. 16, 1996.
Non-Final Office Action from Reexamination Control No. 90/008,588, (Reexamination of U.S. Pat. No. 5,632,676, U.S. Appl. No. 08/134,995), dated Nov. 1, 2007.
Request for Reexamination of U.S. Pat. No. 6,010,729, Control No. 90/008,879, filed Oct. 15, 2007.
Hruska and Tocik, "Fungicidal Effect of Peracetic Acid on Meat Microflora" (1965) pp. 215-217.
Amendment in Response to Non-Final Office Action from U.S. Appl. No. 10/370,798, filed on Oct. 16, 2007.
Declaration of Stephen P. Safranski in Support of Ecolab's Motions (1) To Amend Judgment, (2) For a Permanent Injunction Against Infringement, (3) For Enhanced Damages, (4) For Attorney Fees, (5) For an Award of Interest, (6) For an Accounting and (7) For Judgment as a Matter of Law, filed Dec. 11, 2007.
FMC's Consolidated Memorandum of Law in Support of its Post-Trial Motions, filed Dec. 11, 2007.
Ecolab's Memorandum of Law in Opposition to FMC's Motions for Judgment as a Matter of Law and to Amend Judgment, filed Dec. 21, 2007.
Declaration of Frances M. McCloskey in Opposition to FMC Corporation's Motion to Amend Judgment, filed Dec. 21, 2007.
Declaration of Stephen P. Safranski in Support of Ecolab's Memorandum of Law in Opposition to FMC's Motions for Judgment as a Matter of Law and to Amend Judgment, filed Dec. 21, 2007.
FMC's Memorandum of Law in Opposition to Ecolab's Post-Trial Motions, filed Dec. 21, 2007.
Declaration of John M. Rovison, Jr., filed Dec. 21, 2007.
Order (Denying Post Trial Motions), filed Feb. 22, 2008.
Notice of Appeal by Ecolab, filed Feb. 28, 2008.
Notice of Appeal by FMC Corporation, filed Mar. 10, 2008.
Ecolab's Memorandum of Law in Support of Emergency Motion for an Injunction Pending Appeal, filed Mar. 10, 2008.
Court Docket from PACER for *Ecolab, Inc.* v. *FMC Corporation*, U.S. District Court for the District of Minnesota, Case No. 0:05-cv-00831-JMR-FLN, docket accessed Mar. 24, 2008.
Court Docket from PACER for *Ecolab, Inc.* v. *FMC Corporation*, U.S. Court of Appeals for the Federal Circuit, Case No. 2008-1228, docket accessed Mar. 25, 2008.
Order Granting Request for Reexamination of U.S. Pat. No. 6,010,729, Control No. 90/008,879, dated Jan. 11, 2008.
Request for Reexamination of U.S. Pat. No. 6,010,729, Control No. 90/009,066, filed on Mar. 3, 2008.
Request for Reexamination of U.S. Pat. No. 6,103,286, Control No. 90/009,065, filed on Mar. 3, 2008.
Request for Reexamination of U.S. Pat. No. 6,113,963, Control No. 90/009,068, filed on Mar. 3, 2008.
Response to Non-Final Rejection from the Reexamination of U.S. Pat. No. 5,632,676, Control No. 90/008,588, filed Jan. 2, 2008.
Supplemental Communication from the Reexamination of U.S. Pat. No. 5,632,676, Control No. 90/008,588, filed Jan. 16, 2008.
Interview Summary from the Reexamination of U.S. Pat. No. 5,632,676, Control No. 90/008,588, filed Mar. 17, 2008.
Final Office Action from U.S. Appl. No. 10/370,798, dated Jan. 10, 2008.
Wofasteril 400 (40% peracetic acid solution) Safety Data Sheet.
MSDS, FMC Corporation's 15% (15/10) PAA.
MSDS, FMC Corporation's 15% (15/23) PAA.
MSDS, FMC Corporation's 5% PAA.
Proxitane® 5:14 Product Data Sheet.
Stryer, Biochemistry, 3$^{rd}$ ed., (1988) W.H. Freeman & Co. New York, Chapter 17.
FMC's Preliminary Claim Construction Submission, Mar. 24, 2006.
Expert Report of R. Bruce Tompkin, Sep. 1, 2006 [Redacted].
Rebuttal Expert Report of Scott M. Russell, Ph.D., Sep. 29, 2006 [Redacted].
Complaint, from *FMC Corporation* v. *B. Eugene Guthery*, Civ. No. 05409 (D. N.J. filed Nov. 12, 2007).
Complaint, from *B. Eugene Guthery* v. *FMC Corporation*, Civ. No. 186 (E.D. Tex. filed Dec. 13, 2007).
Statement of Substance of Examiner Interview from the Reexamination of U.S. Pat. No. 6,010,729, Control No. 90/008,879, filed on Apr. 9, 2008.
Order Granting Request for Reexamination of U.S. Pat. No. 6,010,729, Control No. 90/009,066, dated May 20, 2008.
Order Granting Request for Reexamination of U.S. Pat. No. 6,103,286, Control No. 90/009,065, dated May 22, 2008.
Order Granting Request for Reexamination of U.S. Pat. No. 6,113,963, Control No. 90/009,068, dated May 20, 2008.
Examiner Interview Summary from the Reexamination of U.S. Pat. No. 5,632,676, Control No. 90/008,588, dated Feb. 26, 2008.
Notice of Intent to Issue Ex Parte Reexamination Certificate, from the Reexamination of U.S. Pat. No. 5,632,676, Control No. 90/008,588, dated May 20, 2008.
FMC's Memorandum of Law in Opposition to Ecolab's Emergency Motion for an Injunction Pending Appeal, filed Mar. 26, 2008.
Declaration of Alan M. Anderson in Support of Opposition to Ecolab's Emergency Motion for an Injunction Pending Appeal, filed Mar. 26, 2008.
Order (Denying Motion for Preliminary Injunction), filed Apr. 2, 2008.
Court Docket from PACER for *Ecolab, Inc.* v. *FMC Corporation*, U.S. District Court for the District of Minnesota, Case No. 0:05-cv-00831-JMR-FLN, docket accessed May 27, 2008.
Brief of Appellant Ecolab Inc., filed May 9, 2008.
Court Docket from PACER for *Ecolab, Inc.* v. *FMC Corporation*, U.S. Court of Appeals for the Federal Circuit, Case No. 2008-1228, docket accessed May 27, 2008.
Decision Merging Reexamination Proceedings, from 90/008,593 and 90/009,068, dated Jul. 19, 2008.
RCE and Amendment After Final Action Under 37 C.F.R. 1.116, from U.S. Appl. No. 10/370,798, filed on Jul. 10, 2008.
Restriction Requirement, from U.S. Appl. No. 11/894,334, dated Jun. 5, 2008.
Court Docket from PACER for *Ecolab, Inc.* v. *FMC Corporation*, U.S. District Court for the District of Minnesota, Case No. 0:05-cv-00831-JMR-FLN, docket accessed Aug. 19, 2008.
Brief for Defendant-Cross Appellant FMC Corporation, filed Jun. 23, 2008.
Response and Reply Brief of Appellant Ecolab Inc., filed Aug. 4, 2008.
Court Docket from PACER for *Ecolab, Inc.* v. *FMC Corporation*, U.S. Court of Appeals for the Federal Circuit, Case No. 2008-1228, docket accessed Aug. 19, 2008.
Reply Brief for Defendant-Cross Appellant FMC Corporation, filed Aug. 21, 2008.
Decision Merging Reexamination Proceedings from 90/008,592, 90/008,879, and 90/009,066, dated Oct. 7, 2008.
Non-Final Office Action from Control Nos. 90/008,592, 90/008,879, and 90/009,066, dated Oct. 30, 2008.
Decision Merging Reexamination Proceedings from 90/008,587 and 90/009,065, dated Sep. 26, 2008.
Notice of Intent to Issue Reexamination Certificate from 90/008,587 and 90/009,065, dated Nov. 14, 2008.
Non-Final Office Action from Control Nos. 90/008,593 and 90/009,068, dated Oct. 29, 2008.
Non-Final Office Action from U.S. Appl. No. 10/370,798, dated Oct. 6, 2008.
Response to Restriction Requirement from U.S. Appl. No. 11/894,334, filed on Nov. 5, 2008.
Joint Appendix (with Exhibits), filed Aug. 28, 2008.
FMC Corporation's Supplemental Appendix (with Exhibits), filed Oct. 10, 2008.

(56) References Cited

OTHER PUBLICATIONS

Court Docket from PACER for *Ecolab, Inc. v. FMC Corporation*, U.S. District Court for the District of Minnesota, Case No. 0:05-cv-00831-JMR-FLN, docket accessed Dec. 3, 2008.
Court Docket from PACER for *Ecolab, Inc. v. FMC Corporation*, U.S. Court of Appeals for the Federal Circuit, Case No. 2008-1228, docket accessed Dec. 3, 2008.
Examiner Interview Summary from Control Nos. 90/008,592, 90/008,879, and 90/009,066, dated Dec. 9, 2008.
Examiner Interview Summary from Control Nos. 90/008,592, 90/008,879, and 90/009,066, dated Dec. 16, 2008.
Amendment in Response to Office Action from Control Nos. 90/008,592, 90/008,879, and 90/009,066, filed on Dec. 30, 2008.
Supplemental Amendment in Response to Office Action from Control Nos. 90/008,592, 90/008,879, and 90/009,066, filed on Jan. 2, 2008.
Declaration of Timothy A. Gutzmann Under 37 C.F.R. § 1.132, from Control No.'s 90/008,592, 90/008,879, and 90/009,066, dated Dec. 24, 2008.
Examiner Interview Summary from Control Nos. 90/008,593 and 90/009,068, dated Dec. 9, 2008.
Examiner Interview Summary from Control Nos. 90/008,593 and 90/009,068, dated Dec. 16, 2008.
Amendment in Response to Office Action from Control No.'s 90/008,593 and 90/009,068, filed on Dec. 29, 2008.
Declaration of Timothy A. Gutzmann Under 37 C.F.R. § 1.132, from Control No.'s 90/008,593 and 90/009,068, dated Dec. 24, 2008.
Swern, ed., Organic Peroxides vol. 1, (1970) Chapter VI, pp. 313-474.
Product Insert for EM Quant Peracetic Acid Test Strips, dated Nov. 17, 2008.
PML Microbiologicals TDS Phosphate Buffer ph 7.2, dated Aug. 2008.
Ecolab's Material Safety Data Sheets for Inspexx 100 and 200.
Russell, "Processing Tip . . . Efficacy of Antimicrobial Products Used During Processing" in The University of Georgia, Cooperative Extension Service (Sep. 1999).
Russell, "Managing Antimicrobials and Application Systems" (Aug. 29, 2007) from http://www.wattpoultry.com.
FMC Expert Dr. Russell trial testimony excerpt, A6070, 1595:18/1596:3.
Cutter and Dorsa, Journal of Food Protection (1995) 58(12):1294-1296.
De Wit et al., J. Hyg. (1979) 83:27-32.
Rocha et al., Journal of Molecular Catalysis A: Chemical (2002) 186:127-133.
Sawaki and Ogata, "The Kinetics of the Acid-Catalyzed Formation of Peracetic Acid from Acetic Acid and Hydrogen Peroxide" (1965) 38(12):2103-2106.
Zhao et al., The Chinese Journal of Process Engineering (2008) 8:35-41.
Zhao et al., Journal of Molecular Catalysis A: Chemical (2007) 271:246-252.
Court Docket from PACER for *Ecolab, Inc. v. FMC Corporation*, U.S. District Court for the District of Minnesota, Case No. 0:05-cv-00831-JMR-FLN, docket accessed Jan. 22, 2009.
Court Docket from PACER for *Ecolab, Inc. v. FMC Corporation*, U.S. Court of Appeals for the Federal Circuit, Case No. 2008-1228, docket accessed Jan. 22, 2009.
Trial Transcript from *Ecolab, Inc. v. FMC Corporation*, U.S. District Court for the District of Minnesota, Case No. 0:05-cv-00831-JMR-FLN, vol. I, Sep. 24, 2007.
Trial Transcript from *Ecolab, Inc. v. FMC Corporation*, U.S. District Court for the District of Minnesota, Case No. 0:05-cv-00831-JMR-FLN, vol. II, Sep. 25, 2007.
Trial Transcript from *Ecolab, Inc. v. FMC Corporation*, U.S. District Court for the District of Minnesota, Case No. 0:05-cv-00831-JMR-FLN, vol. II, Sep. 27, 2007.
Trial Transcript from *Ecolab, Inc. v. FMC Corporation*, U.S. District Court for the District of Minnesota, Case No. 0:05-cv-00831-JMR-FLN, vol. IV, Sep. 28, 2007.
Trial Transcript from *Ecolab, Inc. v. FMC Corporation*, U.S. District Court for the District of Minnesota, Case No. 0:05-cv-00831-JMR-FLN, vol. V, Oct. 1, 2007.
Trial Transcript from *Ecolab, Inc. v. FMC Corporation*, U.S. District Court for the District of Minnesota, Case No. 0:05-cv-00831-JMR-FLN, vol. VI, Oct. 10, 2007.
Trial Transcript from *Ecolab, Inc. v. FMC Corporation*, U.S. District Court for the District of Minnesota, Case No. 0:05-cv-00831-JMR-FLN, vol. VII, Oct. 11, 2007.
Trial Transcript from *Ecolab, Inc. v. FMC Corporation*, U.S. District Court for the District of Minnesota, Case No. 0:05-cv-00831-JMR-FLN, vol. VIII, Oct. 19, 2007.
Trial Transcript from *Ecolab, Inc. v. FMC Corporation*, U.S. District Court for the District of Minnesota, Case No. 0:05-cv-00831-JMR-FLN, vol. IX, Oct. 23, 2007.
Trial Transcript from *Ecolab, Inc. v. FMC Corporation*, U.S. District Court for the District of Minnesota, Case No. 0:05-cv-00831-JMR-FLN, vol. X, Oct. 30, 2007.
Non-Final Office Action from U.S. Appl. No. 11/894,334, dated Jan. 14, 2009.
Request for Ex Parte Reexamination of U.S. Pat. No. 6,010,729, filed on Mar. 20, 2009.
Second Declaration of John M. Rovison, dated Mar. 20, 2009.
Request for Ex Parte Reexamination of U.S. Pat. No. 6,113,963, filed on Mar. 20, 2009.
Amendment in Response to Non-Final Office Action from U.S. Appl. No. 10/370,798, filed Apr. 3, 2009.
Order Granting Request for Reexamination of U.S. Pat. No. 6,010,729, Control No. 90/010,462, mailed on Apr. 28, 2009.
Order Granting Request for Reexamination of U.S. Pat. No. 6,113,963, Control No. 90/010,463, mailed on Apr. 28, 2009.
Protest Under 37 C.F.R. 1.291 from U.S. Appl. No. 11/894,334, filed May 7, 2009.
Decision from *Ecolab, Inc. v. FMC Corporation*, U.S. Court of Appeals for the Federal Circuit, Case No. 2008-1228 and 2008-1252, decided Jun. 9, 2009.
Court Docket from Pacer for *Ecolab, Inc. v. FMC Corporation*, U.S. Court of Appeals for the Federal Circuit, Case No. 2008-1228, docket accessed Jun. 11, 2009.
Decision Merging Reexamination Proceedings from Control Nos. 90/008,592, 90/008,879, 90/009,066, and 90/010,462, dated Jun. 19, 2009.
Housekeeping Amendment for Merged Reexamination Proceedings from Control Nos. 90/008,592, 90/008,879, 90/009,066, and 90/010,462, filed Jun. 25, 2009.
Second Supplemental Amendment from Control Nos. 90/008,592, 90/008,879, 90/009,066, and 90/010,462, filed Jul. 9, 2009.
Third Supplemental Amendment from Control Nos. 90/008,592, 90/008,879, 90/009,066, and 90/010,462, filed Jul. 10, 2009.
Decision Merging Reexamination Proceedings from Control Nos. 90/008,593, 90/009,068, and 90/010,463, dated Jun. 19, 2009.
Housekeeping Amendment for Merged Reexamination Proceedings from Control Nos. 90/008,593, 90/009,068, and 90/010,463, filed Jun. 25, 2009.
Second Supplemental Amendment from Control Nos. 90/008,593, 90/009,068, and 90/010,463, filed Jul. 9, 2009.
Third Supplemental Amendment from Control Nos. 90/008,593, 90/009,068, and 90/010,463, filed Jul. 10, 2009.
Non-Final Office Action from 10/370,798, dated Jul. 10, 2009.
Supplemental Amendment from U.S. Appl. No. 11/894,334, filed on Jun. 29, 2009.
Notice of Intent to Issue Reexamination Certificate from Control No. 90/008,592, Control No. 90/008,879, Control No. 90/009,066, and Control No. 90/010,462, dated Aug. 20, 2009.
Notice of Intent to Issue Reexamination Certificate from Control No. 90/008,593, Control No. 009,068, and Control No. 90/010,463, dated Aug. 20, 2009.

(56) References Cited

OTHER PUBLICATIONS

Combined Petition for Panel Rehearing & Rehearing En Banc for Plaintiff-Appellant Ecolab Inc., from the United States Court of Appeals for the Federal Circuit, Case No. 2008-1228, 2008-1252, filed Jul. 23, 2009.
FMC Corporation's Response to a Certain Limited Part of the Petition for Rehearing and for Rehearing En Banc filed by Ecolab, Inc., from the United States Court of Appeals for the Federal Circuit, Case No. 2008-1228, 2008-1252, filed Aug. 5, 2009.
Court Docket from PACER for *Ecolab, Inc.* v. *FMC Corporation*, U.S. Court of Appeals for the Federal Circuit, Case No. 2008-1228, 2008-1252, docket accessed Sep. 3, 2009.
Amendment in Response to Non-Final Office Action from U.S. Appl. No. 10/370,798, filed Aug. 21, 2009.
Ex Parte Reexamination Certificate for U.S. Pat. No. 6,010,729, dated Mar. 2, 2010.
Ex Parte Reexamination Certificate for U.S. Pat. No. 6,113,963, dated Dec. 1, 2009.
Non-Final Office Action from U.S. Appl. No. 10/370,798, dated Dec. 1, 2009.
Amendment in Response to Non-Final Office Action from U.S. Appl. No. 10/370,798, filed Jun. 1, 2010.
Non-Final Office Action from U.S. Appl. No. 10/370,798, dated Aug. 6, 2010.
Amendment in Response to Non-Final Office Action from U.S. Appl. No. 10/370,798, filed Nov. 5, 2010.
Non-Final Office Action from U.S. Appl. No. 11/894,334, dated Sep. 25, 2009.
Amendment in Response to Non-Final Office Action from U.S. Appl. No. 11/894,334, filed Mar. 25, 2010.
Final Office Action from U.S. Appl. No. 11/894,334, dated Jun. 18, 2010.
Request for Continued Examination for U.S. Appl. No. 11/894,334, filed Dec. 20, 2010.
Non-Final Office Action for U.S. Appl. No. 10/370,798, dated Feb. 1, 2011.
Ex Parte Quayle Action for U.S. Appl. No. 11/894,334, dated Feb. 25, 2011.
Response to Ex Parte Quayle Action for U.S. Appl. No. 11/894,334, filed Apr. 15, 2011.
Response to Non-Final Office Action for U.S. Appl. No. 10/370,798, filed Apr. 15, 2011.
Notice of Allowance for U.S. Appl. No. 10/370,798, dated Jul. 1, 2011.
Notice of Allowance for U.S. Appl. No. 11/894,334, dated Jul. 1, 2011.
Restriction Requirement for U.S. Appl. No. 13/215,124, dated Aug. 24, 2012.
Meat Decontamination—the State of the Art, Dr. Robin L. Joseph (Ed.), University of Bristol (1997) pp. 1, 8-9, 12, 33-35, 38, 43, 64-91, 98-99 and 104-105.
Request for Inter Partes Reexamination for U.S. Pat. No. 8,030,351, filed Sep. 13, 2012.
Order Granting Request for Inter Partes Reexamination for U.S. Pat. No. 8,030,351, dated Dec. 7, 2012.
Office Action for U.S. Appl. No. 95/002,223, dated Jan. 4, 2013.
Response to Office Action for U.S. Appl. No. 95/002,223, filed Mar. 4, 2013.
Office Action for U.S. Appl. No. 13/215,124, dated Mar. 6, 2013.
Third Part Requestor Comments for U.S. Appl. No. 95/002,223, filed Apr. 2, 2013.
Notice Re Defective Paper for U.S. Appl. No. 95/002,223, dated Apr. 5, 2013.
Response to Office Action for U.S. Appl. No. 95/002,223, dated Apr. 16, 2013.
(Resubmitted) Third Part Requestor Comments for U.S. Appl. No. 95/002,223, filed May 15, 2013.
Response to Office Action for U.S. Appl. No. 13/215,124, filed Sep. 6, 2013, 16 pages.
Final Office Action for U.S. Appl. No. 13/215,124, dated Nov. 25, 2013, 10 pages.
Request for Continued Examination for U.S. Appl. No. 13/215,124, filed May 23, 2014, 9 pages.
Office Action for U.S. Appl. No. 13/215,124, dated Jul. 14, 2014, 9 pages.
Response to Office Action for U.S. Appl. No. 13/215,124, filed Jan. 14, 2015, 7 pages.
Final Office Action for U.S. Appl. No. 13/215,124, issued Mar. 10, 2015, 7 pages.
Request for Continued Examination for U.S. Appl. No. 13/215,124, filed Sep. 10, 2015, 11 pages.
Final Office Action for U.S. Appl. No. 13/215,124, dated Sep. 23, 2015, 7 pages.
Request for Continued Examination for U.S. Appl. No. 13/215,124, filed Jan. 25, 2016, 14 pages.
Final Office Action for U.S. Appl. No. 13/215,124, dated Mar. 22, 2016, 7 pages.
Response to Final Office Action for U.S. Appl. No. 13/215,124, filed Jun. 22, 2016, 19 pages.
Action Closing Prosecution for U.S. Appl. No. 95/002,223, mailed Jul. 9, 2014, 109 pages.
Amendment in response to Action Closing Prosecution in *Inter Partes* Reexamination for U.S. Appl. No. 95/002,223, filed Aug. 11, 2013, 290 pages. (Including Exhibits 1-8).
Corrected Amendment in Response to Action Closing Prosecution in *Inter Partes* Reexamination for U.S. Appl. No. 95/002,223, filed Aug. 13, 2013, 62 pages.
*Inter Partes* Reexamination Certificate for U.S. Pat. No. 8,030,351, dated Aug. 19, 2015, 2 pages.
Requestor Comments in Response to "Amendment in Response to Action Closing Prosecution in *Inter Partes* Reexamination" for U.S. Appl. No. 95/002,223, filed Sep. 10, 2014, 63 pages. (Including Exhibits 15-21).
Right of Appeal Notice for U.S. Appl. No. 95/002,223, dated Mar. 23, 2015, 119 pages.
Non-final Rejection for U.S. Appl. No. 13/216,133, dated Nov. 30, 2012, 9 pages.
Response to Non-final Rejection for U.S. Appl. No. 13/216,133, filed May 30, 2013, 7 pages.
Non-final Rejection for U.S. Appl. No. 13/216,133, dated Aug. 8, 2013, 10 pages.
Response to Non-final Rejection for U.S. Appl. No. 13/216,133, filed Feb. 10, 2014, 16 pages.
Final Rejection for U.S. Appl. No. 13/216,133, dated May 8, 2014, 16 pages.
Request for Continued Examination for U.S. Appl. No. 13/216,133, filed Nov. 7, 2014, 10 pages.
Final Rejection for U.S. Appl. No. 13/216,133, dated Dec. 5, 2014, 6 pages.
Request for Continued Examination for U.S. Appl. No. 13/216,133, filed Jun. 6, 2015, 11 pages.
Final Rejection for U.S. Appl. No. 13/216,133, dated Jul. 13, 2015, 6 pages.
Request for Continued Examination for U.S. Appl. No. 13/216,133, filed Jan. 12, 2016, 15 pages.
Non-Final Rejection for U.S. Appl. No. 13/216,133, dated Mar. 9, 2016, 9 pages.
Response to Non-Final Rejection for U.S. Appl. No. 13/216,133, filed Jul. 5, 2016, 15 pages.
Notice of Allowance for U.S. Appl. No. 13/216,133, dated Sep. 8, 2016, 7 pages.
Notice of Allowance for U.S. Appl. No. 13/216,133, dated Sep. 19, 2016, 5 pages.
Request for Continued Examination for U.S. Appl. No. 13/216,133, filed Nov. 10, 2016, 3 pages.
Response after final action for U.S. Appl. No. 13/216,133, filed Nov. 14, 2016, 13 pages.
Notice of Allowance for U.S. Appl. No. 13/216,133, dated Dec. 12, 2016, 5 pages.

* cited by examiner

TREATMENT OF ANIMAL CARCASSES

CROSS-REFERENCE TO RELATED APPLICATIONS

This application is a continuation of U.S. Ser. No. 13/216,133, filed 23 Aug. 2011, which is a continuation of U.S. Ser. No. 11/894,334, filed 20 Aug. 2007, now U.S. Pat. No. 8,030,351, which is a continuation of U.S. Ser. No. 10/370,798, filed 20 Feb. 2003, now U.S. Pat. No. 8,043,650, which is a continuation of U.S. Ser. No. 10/084,697, filed 28 Feb. 2002, now U.S. Pat. No. 6,545,047, which is a continuation of U.S. Ser. No. 09/634,502, filed 9 Aug. 2000, now abandoned, which is a divisional of U.S. Ser. No. 09/419,019, filed 15 Oct. 1999, now U.S. Pat. No. 6,103,286, which is a divisional of U.S. Ser. No. 09/137,242, filed 20 Aug. 1998, now U.S. Pat. No. 6,010,729. The content of each of these applications is incorporated herein by reference for all purposes.

FIELD OF THE INVENTION

The invention generally relates to compositions and processes for cleaning or sanitizing animal carcasses during meat packing or preparation. More specifically, this invention relates to antimicrobial compositions and processes for cleaning and sanitizing animal carcasses through direct contact between the carcass and the treatment. The nature of the contact between the carcass and the antimicrobial compositions improves antimicrobial properties. The compositions and methods reduce microbial populations and do not affect the appearance, smell or taste of the carcass meat.

BACKGROUND OF THE INVENTION

The cleaning of carcasses in the preparation of any food product can be an unsanitary and time consuming task. Further, without a cleaning routine which follows an ordered process of steps to completely sanitize carcass meat, any number of problems may arise. Carcass meat may retain pathogens or infectious microbes (*E. coli*) or become increasingly more contaminated if viscera is allowed to rupture or is not properly removed. Further, incomplete cleaning of the carcass meat may also result in the presence of infectious microbes making the meat unsuitable for consumption.

PURAC® is a natural lactic acid produced by fermentation from sugar. It has a mild acid taste and is widely used in the food industry as an acidulant. PURAC® is an effective decontaminating agent for use with poultry, beef and pork carcasses and slaughter by-products. PURAC® is most effective at a use concentration of between 1 and 2 percent, and can be used at several different points in the slaughter line. Application immediately after hide removal reduces the amount of microorganisms entering subsequent processing steps, while treatments after evisceration and prior to chilling have the greatest residual effects. Mountney et al. also discuss the use of lactic acid to lower bacterial counts and otherwise preserve poultry in "Acids As Poultry Meat Preservatives" in Poultry Science, 44: 582, 1965. Blankenship et al. discussed the destruction of *Salmonella* contaminates on fajita chicken meat in "Efficacy of Acid Treatment Plus Freezing To Destroy *Salmonella* Contaminates Of Spice Coated Chicken Fajita Meat" in Poultry Science, Vol. 69, Supp., 1990, p. 20. Adams et al. discuss the use of propylene glycol, sodium lactate, and lactic acid in chill water to reduce *salmonella* contamination of processed broilers.

(See, *Effects of Various Chill Water Treatments on Incidents and Levels of Salmonella on Processed Carcasses*, Department of Animal and Poultry Sciences, University of Arkansas, Fayetteville). Izat et al. discuss the effects of lactic acid on commercial broiler carcasses in reducing *salmonella* counts in Poultry Science, Vol. 69, Supp. 1990, p. 152; Journal of Quality, Vol. 13, 1990). 295-306; and Journal of Food Protection, Vol. 52, No. 9, pp. 670-673, September 1989. Avens et al. discuss the pasteurization of turkey carcasses and the reduction of *salmonella* using lactic acid in Poultry Science, Vol. 51, 1972, p. 1781. Mulder et al. in 1987 Poultry Science 66:1555-1557 reports a study of treating broiler carcasses with lactic acid, 1-cysteine and hydrogen peroxide. The treatment with lactic acid and hydrogen peroxide resulted in a 4-log cycle reduction in colony forming units of *Salmonella tphimurium*. Nevertheless, use of lactic acid resulted in a slightly changed color of the carcasses and all the treatments with hydrogen peroxide resulted in bleached and bloated carcasses.

Although peroxycarboxylic acids are known to be used for cleaning and sanitizing equipment and other surfaces, they have not been reported for cleaning and sanitizing animal carcasses. Holzhauer et al., U.S. Pat. No. 5,435,808, describes curing of animal hides with an acetic acid, peroxyacetic acid, hydrogen peroxide, and phosphoric acid combination. The heightened concerns of consumers over the organoleptic purity and safety of meat products, concerns over the environmental and organoleptic impact of many antimicrobial agents currently available, as well as the stringent economies of the meat and poultry industry have resulted in an ongoing need for carcass sanitizing compositions and processes which provide increased sanitization with organoleptic and environmental purity.

SUMMARY OF THE INVENTION

Accordingly the present invention, in a first aspect, provides a method of treating animal carcasses to obtain a reduction by at least one $\log_{10}$ in surface microbial population which method includes the step of treating said carcass with an antimicrobial composition comprising an effective antimicrobial amount comprising at least 2 parts per million (ppm, parts by weight per each one million parts) of one or more peroxycarboxylic acids having up to 12 carbon atoms and an effective antimicrobial amount comprising at least 20 ppm of one or more carboxylic acids having up to 18 carbon atoms to reduce the microbial population.

A second aspect of the invention is an antimicrobial composition adapted for cleaning and sanitizing animal carcasses which contains about 0.5 weight percent (wt-%) to about 20 wt-% of a mixture of one or more peroxycarboxylic acids having from 2-4 carbon atoms, and one or more peroxycarboxylic acids having from 8-12 carbon atoms, from about 0.5 wt-% to about 60 wt-% of an alpha-hydroxy mono or dicarboxylic acid having 3-6 carbon atoms, an effective amount of a sequestrant and an effective amount of a hydrotrope.

A third preferred aspect of the present invention is an antimicrobial composition adapted for treating animal carcasses consisting of a mixture of peroxyacetic and peroxyoctanoic acid in a ratio of about 10:1 to about 1:1, from about 0.1 to about 10 wt-% of lactic acid, from about 4 wt-% to about 10 wt-% of hydrogen peroxide and from about 0.5 wt-% to about 1.5 wt-% of a sequestering agent.

A fourth aspect of the present invention involves a method of treating an animal carcass to reduce a microbial population in resulting cut meat, the method comprising the steps of spraying an aqueous antimicrobial treatment composition onto said carcass at a pressure of at least 50 psi at a temperature of up to about 60° C. resulting in a contact time of at least 30 seconds, the antimicrobial composition comprising an effective antimicrobial amount comprising least 2 ppm of one or more carboxylic acid, peroxycarboxylic acid or mixtures thereof; and achieving at least a one $\log_{10}$ reduction in the microbial population.

A fifth aspect of the present invention involves a method of treating an animal carcass to reduce a microbial population resulting cut meat, the method comprising the steps of placing the carcass in a chamber at atmospheric pressure; filling the chamber with condensing steam comprising an antimicrobial composition for a short duration; and quickly venting and cooling the chamber to prevent browning of the meat carcass; wherein the duration of the steam thermal process may be from about 5 seconds to about 30 seconds and the chamber temperature may reach from about 50° C. to about 93° C.

The antimicrobial composition can be applied in various ways to obtain intimate contact with each potential place of microbial contamination. For example, it can be sprayed on the carcasses, or the carcasses can be immersed in the composition. Additional methods include applying a foamed composition and a thickened or gelled composition. Vacuum and or light treatments can be included, if desired, with the application of the antimicrobial composition. Thermal treatment can also be applied, either pre-, concurrent with or post application of the antimicrobial composition. We have found a preferred spray method for treating carcasses with compositions of the invention involving spraying the carcass with an aqueous spray at a temperature less than about 60° C. at a pressure of about 50 to 500 psi gauge wherein the spray comprises an effective antimicrobial amount of a carboxylic acid, an effective antimicrobial amount of a peroxycarboxylic acid or mixtures thereof. These sprays can also contain an effective portion of a peroxy compound such as hydrogen peroxide and other ingredients such as sequestering agents, etc. We have found that the high pressure spray action of the aqueous treatment removes microbial populations by combining the mechanical action of the spray with the chemical action of the antimicrobial materials to result in a surprisingly improved reduction of such populations on the surface of the carcass. All pressures are psig (or psi gauge). Differentiation of antimicrobial "-cidal" or "-static" activity, the definitions which describe the degree of efficacy, and the official laboratory protocols for measuring this efficacy are important considerations for understanding the relevance of antimicrobial agents in compositions. Antimicrobial compositions may effect two kinds of microbial cell damages. The first is a truly lethal, irreversible action resulting in complete microbial cell destruction or incapacitation. The second type of cell damage is reversible, such that if the organism is rendered free of the agent, it can again multiply. The former is termed bacteriocidal and the latter, bacteriostatic. A sanitizer and a disinfectant are, by definition, agents which provide antibacterial or bacteriocidal activity and achieve at least a five fold reduction (i.e., a five log 10 reduction) in microbial populations after a 30 second contact time (see AOAC method 960.09).

In contrast, a preservative is generally described as an inhibitor or bacteriostatic composition that simply retards growth in a reversible mode. For the purpose of this patent application, successful microbial reduction is achieved when the microbial populations are reduced by one $\log_{10}$). In this industry, the one $\log_{10}$ microbial population reduction is the minimum acceptable for the processes. Any increased reduction in microbial population is an added benefit that provides higher levels of protection for processed carcass meat.

DETAILED DESCRIPTION OF THE INVENTION

The invention is a process for sanitizing animal carcasses through treatment with aqueous streams containing an antimicrobial composition. The dip or spray methods used for carcass cleaning as well as sanitizing animal carcasses generally include an effective antimicrobial concentration of one or more carboxylic acids and one or more peroxycarboxylic acids.

A. The Sanitizing Composition

The sanitizing composition used in the method of the invention generally contains one or more carboxylic acids and one or more peroxycarboxylic acids with a peroxygen compound such as $H_2O_2$. Typically, however, the composition contains one or more carboxylic acids, an oxidizer, and one or more peroxycarboxylic acids depending on equilibrium. Commonly, the peroxycarboxylic acid material can be made by oxidizing a carboxylic acid directly to the peroxycarboxylic acid material which is then solubilized in the aqueous rinse agent compositions of the invention. Further, the materials can be made by combining the unoxidized acid with a peroxygen compound such as hydrogen peroxide to generate the peracid in situ prior to blending the peroxycarboxylic acid with other constituents. The compositions of the invention comprises blends of the carboxylic acid and percarboxylic acid along with other components including a peroxy source such as hydrogen peroxide. Once blended and applied the compositions can change due to interactions between the blended materials and due to interactions in the use locus. For example, the salt component can exchange and become associated with free acids and the peroxy source can oxidize oxidizable materials. The antimicrobial properties arise from the blend of an acid material and a peracid material. The modification post blending and application do not change the invention.

A carboxylic acid is an organic acid (R—COOH) which contains an aliphatic group and one or more carboxyl groups. A carboxyl group is represented by —COOH, and is usually located at a terminal end of the acid. The aliphatic group can be a substituted or unsubstituted group. Common aliphatic substituents include —OH, —OR, —NO$_2$, halogen, and other substituents common on these groups. An example of a simple carboxylic acid is acetic acid, which has the formula $CH_3COOH$. A peroxycarboxylic acid is a carboxylic acid which has been oxidized to contain a terminal —COOOH group. The term peroxy acid is often used to represent a peroxycarboxylic acid. An example of a simple peroxy acid is peroxyacetic acid, which has the formula $CH_3COOOH$.

Generally when the peroxycarboxylic acid is formulated in accordance with the invention a monocarboxylic acid, such as acetic acid, is combined with an oxidizer such as hydrogen peroxide. The result of this combination is a reaction producing a peroxycarboxylic acid, such as peroxyacetic acid, and water. The reaction follows an equilibrium in accordance with the following equation:

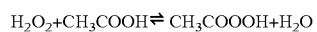

wherein the p$K_{eq}$ is 1.7.

The importance of the equilibrium results from the presence of hydrogen peroxide, the carboxylic acid and the peroxycarboxylic acid in the same composition at the same time. Because of this equilibrium, a mixture of carboxylic acid and peroxycarboxylic acid can be combined in water without adding hydrogen peroxide. If permitted to approach equilibrium, the mixture will evolve hydrogen peroxide. This combination provides enhanced sanitizing with none of the deleterious environmental or organoleptic effects of other sanitizing agents, additives, or compositions.

The Carboxylic Acid

The first constituent of the composition used in the method of the invention includes one or more carboxylic acids. Generally, carboxylic acids have the formula R—COOH wherein the R may represent any number of different groups including aliphatic groups, alicyclic groups, aroma groups, heterocyclic groups, all of which may be saturated or unsaturated. Carboxylic acids also occur having one, two, three, or more carboxyl groups. Aliphatic groups can be further differentiated into three distinct classes of hydrocarbons. Alkanes (or paraffins) are saturated hydrocarbons. Alkenes (or olefins) are unsaturated hydrocarbons which contain one or more double bonds and alkynes (or acetylenes) are unsaturated hydrocarbons containing one or more highly reactive triple bonds. Alicyclic groups can be further differentiated into three distinct classes of cyclic hydrocarbons. Cycloparaffins are saturated cyclic hydrocarbons. Cycloolefins are unsaturated cyclic hydrocarbons which contain one or more double bonds while cycloacetylenes are unsaturated cyclic hydrocarbons containing one or ore highly reactive triple bonds. Aromatic groups are defined as possessing the unsaturated hydrocarbon ring structure representative of benzene. Heterocyclic groups are defined as 5 or 6 member ring structures wherein one or more of the ring atoms are not carbon. An example is pyridine, which is essentially a benzene ring with one carbon atom replaced with a nitrogen atom.

Carboxylic acids have a tendency to acidify aqueous compositions in which they are present as the hydrogen atom of the carboxyl group is active and may appear as a cation. The carboxylic acid constituent within the present composition when combined with aqueous hydrogen peroxide generally functions as an antimicrobial agent as a result of the presence of the active hydrogen atom. Moreover, the carboxylic acid constituent within the invention maintains the composition at an acidic pH. The composition of the invention can utilize carboxylic acids containing as many as 18 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic, neopentanoic, neoheptanoic, neodecanoic, oxalic, malonic, succinic, glutaric, adipic, pimelic and subric acid.

Carboxylic acids which are generally useful are those having one or two carboxyl groups where the R group is a primary alkyl chain having a length of $C_2$ to $C_5$ and which are freely water soluble. The primary alkyl chain is that carbon chain of the molecule having the greatest length of carbon atoms and directly appending carboxyl functional groups. Especially useful are mono- and dihydroxy substituted carboxylic acids including alpha-hydroxy substituted carboxylic acid. A preferred carboxylic acid is acetic acid, which produces peroxyacetic acid to increase the sanitizing effectiveness of the materials. Acetic acid has the structure of the formula:

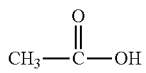

An especially preferred α-hydroxy-monocarboxylic acid is lactic acid, also known as 2-hydroxypropionic acid, which is a naturally occurring organic acid. Lactic acid has a molecular weight of 90.08 and is soluble in water, alcohol, acetone, ether and glycerol. Lactic acid occurs naturally and may be produced by fermentation. Alternatively, lactic acid may be synthesized.

Lactic acid has the structure of the formula

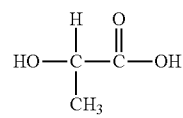

The concentration of α-hydroxy-mono- or di-carboxylic acid useful in the present invention generally ranges from about 0.5 wt-% to about 60 wt-%, preferably about 1 wt-% to about 20 wt-%, and most preferably from about 2 wt-% to about 10 wt-%. This concentration range of lactic acid is preferred for reasons of optimal acidity within the composition, as well as for the optimal antimicrobial efficacy which it brings to the antimicrobial system.

Reducing the concentration of lactic acid in comparison to any given concentration of hydrogen peroxide will essentially reduce the antimicrobial activity of the composition. Moreover, reducing the concentration of lactic acid may result in an increase in the pH of the composition and accordingly raise the potential for decreased antimicrobial activity. In sharp contrast, increasing the concentration of lactic acid within the present composition may tend to increase the antimicrobial activity of the composition. Furthermore, increasing the concentration of lactic acid in the composition of the present invention will tend to decrease the pH of the composition. Preferably, the pH of the present composition will be 4 or less with a generally preferred pH in the composition being between 1.5 and 3.75, and a pH between about 2 and 3.5 being most preferred.

Generally, the concentration of carboxylic acid within the composition used in the process of the invention ranges from about 0.5 wt-% to about 60 wt-%, preferably from about 10 wt-% to about 60 wt-%, and most preferably from about 20 wt-% to about 50 wt-%.

The Peroxycarboxylic Acid

Another principle component of the antimicrobial composition of the invention is an oxidized carboxylic acid. This oxidized or peroxycarboxylic acid provides heightened antimicrobial efficacy when combined with hydrogen peroxide and the monocarboxylic acid in an equilibrium reaction mixture. Peroxycarboxylic acids generally have the formula $R(CO_3H)$, where R is an alkyl, arylalkyl, cycloalkyl, aromatic or heterocyclic group, and n is one or two and named by prefixing the parent acid with peroxy. An alkyl group is a paraffinic hydrocarbon group which is derived from an alkane by removing one hydrogen from the formula. The hydrocarbon group may be either linear or branched, having up to 12 carbon atoms. Simple examples include methyl ($CH_3$) and ethyl ($CH_2CH_3$). An arylalkyl group contains both aliphatic and aromatic structures. A cycloalkyl group is defined as a cyclic alkyl group.

While peroxycarboxylic acids are not very stable, their stability generally increases with increasing molecular weight. Thermal decomposition of these acids may generally proceed by free radical and nonradical paths, by photodecomposition or radical-induced decomposition, or by the action of metal ions or complexes. Peroxycarboxylic acids may be made by the direct, acid catalyzed equilibrium action of 30-98 wt-% hydrogen peroxide with the carboxylic acid, by autoxidation of aldehydes, or from acid chlorides, acid anhydrides, or carboxylic anhydrides with hydrogen or sodium peroxide.

Peroxycarboxylic acids useful in this invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof. These peroxycarboxylic acids have been found to provide good antimicrobial action with good stability in aqueous streams. In a preferred embodiment, the composition of the invention utilizes a combination of several different peroxycarboxylic acids. Preferably, the composition includes one or more small $C_2$-$C_4$ peroxycarboxylic acids and one or more large $C_8$-$C_{12}$ peroxycarboxylic acids. Especially preferred is an embodiment in which the small peroxycarboxylic acid is peroxyacetic acid and the large acid is either peroxyoctanoic acid or peroxydecanoic acid.

Peroxyacetic acid is a peroxycarboxylic acid with a structure as given the formula:

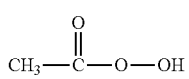

wherein the peroxy group, —O—O—, is considered a high energy bond. Generally, peroxyacetic acid is a liquid having an acrid odor and is freely soluble in water, alcohol, ether, and sulfuric acid. Peroxyacetic acid may be prepared through any number of means known to those of skill in the art including preparation from acetaldehyde and oxygen in the presence of cobalt acetate. A 50% solution of peroxyacetic acid may be obtained by combining acetic anhydride, hydrogen peroxide and sulfuric acid. Other methods of formulation of peroxyacetic acid include those disclosed in U.S. Pat. No. 2,833,813, which is incorporated herein by reference.

Peroxyoctanoic acid has the structure of the formula:

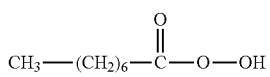

Peroxydecanoic acid has the structure of the formula:

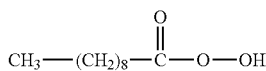

The preferred peroxycarboxylic acid materials of the invention can be used to increase the sanitizing effectiveness of the materials. When a blended acid is used, the peroxycarboxylic acid is blended in proportions that range from about 10:1 to about 1:1 parts of $C_2$-$C_4$ peroxycarboxylic acid per part of $C_8$-$C_{12}$ peroxycarboxylic acid. Preferably, peroxyacetic acid is used at a ratio of about 8 parts per part of peroxyoctanoic acid.

The above sanitizer material can provide antibacterial activity to the rinse aid sanitizers of the invention against a wide variety of microorganisms such as gram positive (for example, *Staphylococcus aureus*) and grain negative (for example, *Escherichia coli*) microorganisms, yeast, molds, bacterial spores, viruses, etc. When combined, the above peroxy acids can have enhanced activity compared to the low molecular weight peroxy acids alone.

Generally, the concentration of peroxycarboxylic acid within the composition used in the process of the invention ranges from about 0.5 wt-% to about 20 wt-%, preferably from about 2 wt-% to about 15 wt-%, and most preferably from about 4 wt-% to about 12 wt-%.

The Oxidizer

The composition used in the method of the invention also includes an oxidizer. Any number of oxidizers may be used as a precursor to the formation of a peroxycarboxylic acid as well as to provide further physical effervescent or agitation action to the composition of the invention. Preferably, the antimicrobial composition of the invention contains hydrogen peroxide. Hydrogen peroxide ($H_2O_2$) has a molecular weight of 34.014 and it is a weakly acidic, clear, colorless liquid. The four atoms are covalently bonded in a non-polar structure:

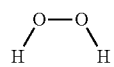

Generally, hydrogen peroxide has a melting point of −0.41° C., a boiling point of 150.2° C., a density at 25° C. of 1.4425 grams per cm$^3$, and a viscosity of 1.245 centipoise at 20° C.

Hydrogen peroxide in combination with the carboxylic acid and peroxycarboxylic acid provides a surprising level of antimicrobial action against microorganisms, even in the presence of high loadings of organic sediment. Additionally, hydrogen peroxide provides an effervescent action which may irrigate any surface to which it is applied. Hydrogen peroxide works with a mechanical flushing action once applied which further plains the surface of application. An additional advantage of hydrogen peroxide is the food compatibility of this composition upon use and decomposition. For example, combinations of peroxyacetic acid and hydrogen peroxide result in acetic acid, water, and oxygen upon decomposition. All of these constituents are food product compatible. Generally, the concentration of hydrogen peroxide within the composition used in the process of the invention ranges from about 1 wt-% to about 35 wt-%, preferably from about 2 wt-% to about 25 wt-%, and most preferably from about 5 wt-% to about 10 wt-%. This concentration of hydrogen peroxide is most preferred as providing optimal antimicrobial effect.

These concentrations of hydrogen peroxide may be increased or decreased while still remaining within the scope of the present invention. For example, increasing the concentration of hydrogen peroxide may increase the antimicrobial efficacy of the claimed invention. Furthermore, increasing the hydrogen peroxide concentration may reduce the need to stabilize the hydrogen peroxide within the composition. Specifically, increasing the hydrogen peroxide concentration in the composition may provide a composition which has extended shelf life.

In contrast, decreasing the concentration of hydrogen peroxide may decrease the antimicrobial efficacy of the composition and necessitate the use of an increased concentration of carboxylic acid. Moreover, decreasing the concentration of hydrogen peroxide may necessitate the use of some stabilizing agent to ensure that the composition of the present invention will remain stable and efficacious over the intended time period.

In all, altering the concentration of the oxidizing agent will effect the equilibrium mix of the peroxycarboxylic acid used in the invention.

The Carrier

The composition of the invention also includes a carrier. The carrier functions to provide a reaction medium for the solubilization of constituents and the production of peroxycarboxylic acid as well as a medium for the development of an equilibrium mixture of oxidizer, peroxycarboxylic acid, and carboxylic acid. The carrier also functions to deliver and wet the antimicrobial composition of the invention to the intended substrate. To this end, the carrier may contain any component or components which will facilitate the functions. Generally, the carrier consists of water which is an excellent solubilizer and medium for reaction and equilibrium. The carrier may also include any number of constituents such as various organic compounds which facilitate the functions provided above. Organic solvents which have be found useful include simple alkyl alcohols such as ethanol, isopropanol, n-propanol, and the like. Polyols are also useful carriers in accordance with the invention, including propylene glycol, polyethylene glycol, glycerol, sorbitol, and the like. Any of these compounds may be used singly or in combination with other organic or inorganic constituents or, in combination with water or in mixtures thereof. Preferably, the carrier consists of from about 1 wt-% to about 60 wt-% of an organic solvent.

Generally, the carrier makes up a large portion of the composition of the invention and may essentially be the balance of the composition apart from the active antimicrobial composition adjuvants, and the like. Here again, the carrier concentration and type depend upon the nature of the composition as a whole, the environmental storage and method of application including concentration of the antimicrobial agent, among other factors. Notably the carrier should be chosen and used at a concentration which does not inhibit the antimicrobial efficacy of the act in the composition of the invention.

B. Adjuvants

The composition of the invention may also optionally include any number of adjuvants which are stable in an oxidizing environment, and add beneficial properties of stability, sequestration, sheeting and rinsing, etc. These adjuvants may be preformulated with the sanitizing agent of the invention or added to the system simultaneously, or even after, the addition of the sanitizing agent of the invention.

Chelating Agent

The sanitizing agents of the invention may also contain a polyvalent metal complexing or chelating agent that aids in reducing the harmful effects of hardness components and service water and improves product stability. The typically harmful effects of calcium, magnesium, iron, manganese, etc., ions present in service water can interfere with the action of either the washing compositions or rinsing compositions or can tend to decompose the active peroxygen sanitizer materials. The chelating agent or sequestering agent can effectively complex and remove such ions from inappropriate interaction with active ingredients thus increasing sanitizing agent performance.

Both organic and inorganic chelating agents may be used. Inorganic chelating agents include such compounds as sodium tripolyphosphate and other higher linear and cyclic polyphosphate species. Organic chelating agents include both polymeric and small molecule chelating agents. Polymeric chelating agents commonly comprise polyanionic compositions such as polyacrylic acid compounds. Amino phosphates and phosphonates are also suitable for use as chelating agents in the compositions of the invention and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms.

Preferred chelating agents for use in this invention include improved food additive chelating agents such as disodium salts of ethylene diamine tetraacetic acid or the well known phosphonates sold in the form of DEQUEST® materials, for example, 1-hydroxyethylidene-1,1-diphosphonic acid, etc. The phosphonic acid may also comprise a low molecular weight phosphonopolycarboxylic acid such as one having about 2-4 carboxylic acid moieties and about 1-3 phosphonic acid groups. Such acids include 1-phosphono-1-methyl-succinic acid, phosphonosuccinic acid and 2-phosphonobutane-1,2,4-tricarboxylic acid. Another organic phosphonic acid is $(CH_3C(PO_3H_2)_2OH)$, available from Monsanto Industrial Chemicals Co., St. Louis, Mo., as DEQUEST® 2010, (which is a 58-62% aqueous solution; amino (tri (methylenephosphonic acid)] $(N[CH_2PO_3H_2]_3)$, available from Monsanto as DEQUEST® 2000, as a 50% aqueous solution; ethylediamine [tetra(methylenephosphonic acid)] available from Monsanto as DEQUEST® 2041, as a 90% solid acid product; and 2-phosphonobutane-1,2,4-tricarboxylic acid available from Mobay Chemical Corporation, Inorganic Chemicals Division, Pittsburgh, Pa., as Bayhibit AM, as a 45-50% aqueous solution.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in the present invention generally ranges from about 0.01 to about 10 wt-%, preferably from about 0.1 to about 5 wt-%, most preferably from about 0.5 to about 2 wt-%.

Hydrotrope

The sanitizing agent of the invention may also include a hydrotrope coupler or solubilizer. Such materials can be used to ensure that the composition remains phase stable and in a single highly active aqueous form. Such hydrotrope solubilizers or couplers can be used at compositions which maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Preferred coupling agents for use in the rinse agents of the invention include n-octane sulfonate and aromatic sulfonates such as an alkyl benzene sulfonate (e.g., sodium xylene sulfonate or naphthalene sulfonate). Many hydrotrope solubilizers independently exhibit some degree of antimicrobial activity at low pH. Such action adds to the efficacy of the invention but is not a primary criterion used in selecting an appropriate solubilizing agent. Since the presence of the peroxycarboxylic acid material in the proteinated neutral state provides beneficial biocidal or sanitizing activity, the coupling agent should be selected not for its independent antimicrobial activity but for its ability to provide effective single phase composition stability in the presence of substantially insoluble peroxycarboxylic acid materials and the more soluble compositions of the invention.

Generally, any number of surfactants may be used consistent with the purpose of this constituent.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include β-N-alkylaminopropionic acids, n-alkyl-β-iminodipropionic acids, imidazoline carboxylates, n-alkylIletaines, amine oxides, sulfobetaines and sultaines.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer comprising an EO block and a PO block, a center block of polyoxypropylene units (PO), and having blocks of polyoxyethylene grated onto the polyoxypropylene unit or a center block of EO with attached PO blocks. Further, this surfactant further blocks of either polyoxyethylene or polyoxypropylene in the molecule. The average molecular weight of useful surfactants ranges from about 1000 to about 40,000 and the weight percent content of ethylene oxide ranges from about 10-80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula R-(EO)$_m$-(PO)$_n$ wherein m is an integer of about 2-10 and n is an integer from about 2-20. R can be any suitable radical such as a straight chain alkyl group having from about 6-20 carbon atoms.

Other useful nonionic surfactants of the invention include capped aliphatic alcohol alkoxylates. These end caps include but are not limited to methyl, ethyl, propyl, butyl, benzyl and chlorine. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant of the invention is a fatty acid alkoxylate wherein the surfactant comprises a fatty acid moiety with an ester group comprising a block of EO a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Thickening/Gelling Agents

Thickeners useful in the present invention are those which do not leave contaminating residue on the surface of application, i.e., constituents which are incompatible with food or other sensitive products in contact areas.

Generally, thickeners which may used in the present invention include natural gums such as xanthan gum. Also useful in the present invention are cellulosic polymers, such as carboxymethyl cellulose. Generally, the concentration of thickener use in the present invention will be dictated by the desired viscosity within the final composition. However, as a general guideline, viscosity of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

C. Formulation

The compositions of invention can be formulated by combining the sanitizing agent materials including other adjuvant components with the materials that form the sanitizer composition, the carboxylic acid or acid blend, hydrogen peroxide and optionally, hydrotrope solubilizer.

The compositions can also be formulated with preformed peroxycarboxylic acids. The preferred compositions of the invention can be made by mixing the carboxylic acid or mixture thereof with an optional hydrotrope solubilizer or coupler, reacting the mixture with hydrogen peroxide and then adding the balance of required ingredients to provide rinsing and sanitizing action.

A stable equilibrium mixture is produced containing the carboxylic acid or blend with hydrogen peroxide and allowing the mixture to stand for 1-7 days at 15° C. or more. With this preparatory method, an equilibrium mixture will be formed containing an amount of hydrogen peroxide, unoxidized acid, oxidized or peroxycarboxylic acid and typically unmodified couplers, solubilizer, or stabilizers.

D. Use Compositions

The invention contemplates a concentrate composition which is diluted to a use solution prior to its utilization as a sanitizer. Primarily for reasons of economics, the concentrate would normally be marketed and an end user would preferably dilute the concentrate with water or an aqueous diluent to a use solution.

The general constituent concentrations of the sanitizing concentrate formulated in accordance with the invention may be found in Table 1:

TABLE 1

| Constituent | Preferred (wt-%) | More Preferred (wt-%) | Most Preferred (wt-%) |
|---|---|---|---|
| $H_2O_2$ | 1-35 | 2-25 | 5-10 |
| Peroxycarboxylic acids | 0.5-20 | 2-15 | 4-12 |
| Carboxylic acid | 0.5-60 | 10-60 | 20-50 |
| Chelating agent | 0.01-10 | 0.01-5 | 0.5-2 |
| Hydrotrope | 0.1-20 | 0.5-10 | 1-4 |
| Thickening agent | 0.1-1.5 | 0.1-1.0 | 0.1-0.5 |
| Carrier | 0-97 | 10-90 | 12-65 |

The level of active components in the concentrate composition is dependent on the intended dilution factor and the desired activity of the peroxycarboxylic acid compound and the carboxylic acid.

Generally, a dilution of about 1 fluid ounce to about 0.5 to 10.0 gallons of water is used for aqueous antimicrobial sanitizing solutions. The composition shown in the preferred column of the Table 1 above would be used in a range from about 12.8 fluid ounce per gallon water to about 1 fluid ounce per 780 gallons of water depending on the desired level of peroxycarboxylic acid and concentration of the peroxycarboxylic acid in the product concentrate.

Higher use dilutions can be employed if elevated use temperature (greater than 25° C.) or extended exposure time (greater than 30 seconds) can be employed. In the typical use locus, the concentrate is diluted with a major proportion of water and used for sanitizing using commonly available tap or service water mixing the materials at a dilution ratio of about 0.1 to about 2 ounces of concentrate per gallon of water.

Aqueous antimicrobial sanitizing use solutions can include at least about 2 ppm, preferably about 10 to about 500 ppm, and more preferably about 100 to about 250 parts per million of the peroxycarboylic acid material; about 20 ppm to about 10,000 ppm, and preferably about 50 ppm to about 1,000 ppm of carboxylic acid; and about 10 to about 1,000 ppm of hydrogen peroxide. The aqueous use solution can further include at least bout 50 ppm, preferably about 500 ppm of the hydrotrope solubilizer, and have a pH in the use solution in the range of about 1 to about 11 preferably about 2 to about 10.

E. Method of Use

During processing of the carcass meat, the carcasses can be contacted with the compositions of the invention in any mode be that insures good contact between the carcass and the composition and at least some minimal mechanical work to result in at least a one $\log_{10}$ reduction, preferably at least a two $\log_{10}$ reduction and more preferably a three $\log_{10}$ reduction in the resident microbial preparation. A five $\log_{10}$ reduction in 30 seconds is a sanitizing treatment.

The invention is applicable to a wide range of possible animal carcasses. For example, the antimicrobial compositions of the invention can be used on muscle meats including beef, pork, veal, buffalo or lamb, sea food including scallops, shrimp, crab, octopus, mussels, squid or lobster and poultry including chicken, turkey, ostrich, game hen, squab or pheasant.

A preferred mode is a pressure spray with the sanitizing solution of the invention. During application of the spray solution on the carcasses, the surface of the carcasses can be moved with mechanical action, preferably agitated, rubbed, brushed, etc. Agitation may be by physical scrubbing of the carcasses, through the action of the spray solution under pressure or by other means. The agitation increases the efficacy of the spray solution in killing micro-organisms, perhaps due to better exposure of the solution into the crevasses or small colonies containing the micro-organisms. The spray solution, before application, may also be heated to a temperature of about 15 to 20° C., preferably about 20 to 50° C. to increase efficacy. After a sufficient amount of time to kill the micro-organisms on the carcasses, the spray solution may be rinsed off the animal carcasses.

Application of the material by spray means can be accomplished using a manual spray wand application, an automatic spray of carcasses moving along a production line using multiple spray heads to ensure complete contact or other spray means. One preferred automatic spray application involves the use of a spray booth. The spray booth substantially confines the sprayed composition to within the parameter of the booth. The production line moves the carcass through the entryway into the spray booth in which the carcass is sprayed on all its exterior surfaces with sprays within the booth. After a complete coverage of the material and drainage of the material from the carcass within the booth, the carcass can then exit the booth in a fully treated form. The spray booth can comprises steam jets that can be used to apply the antimicrobial compositions of the invention. These steam jets can be used in combination with cooling water to ensure that the treatment reaching the carcass surface is less than 65° C., preferably less than 60° C. The temperature of the spray on the carcass is important to ensure that the carcass meat is not substantially altered (cooked) by the temperature of the spray. The spray pattern can be virtually any useful spray pattern.

The spray can comprise a fogged material that leaves a fogging apparatus as a dispersion of fog particles in a continuous atmosphere. Such a spray has no defined pattern. The spray can have a pattern such as a conical spray in which the angle between the perimeter of the spray ranges from less than 180° to about 5°. Other spray patterns can also be useful. We have found that one preferred spray pattern involves a "fan" spray pattern in which the spray exits the spray head in a substantially planar form and the angle between the extent of the planar spray from edge to edge is about 20° or less, preferably about 15° or less. We have found that such a spray is preferred due to the increased mechanical action and efficiency of antimicrobial composition add on to the carcass. When such a narrow angle fan spray is used in a spray cabinet enclosure to treat the carcasses, we have found that the optimum distance between the spray head and the carcass is less than about 100 centimeters, preferably about 20 to 80 centimeters, most preferably about 30 to 50 centimeters. Such a configuration efficiently transfers antimicrobial material to the carcass for efficient reduction of the microbial populations.

There are a number of parameters which need to be considered if spraying is the application method of choice. The first parameter to determine is the pressure at which the composition is sprayed onto the carcass. While spray pressures as low as about 25 psi (gauge) can be used with some valuable results, a higher spray pressure, greater than about 25, 50, 100, 150 psi and more preferably greater than about 200 psi, are effective in reducing the microbial populations due to the mechanical action of the spray on the carcass surface and on the microbial population remaining on the surface of the carcass. The spray action is best at temperatures less that 65° C. While a composition comprising lactic acid has been found to be most effective at low pressure, it has been discovered that equal, if not greater antimicrobial efficacy can be obtained by eliminating the lactic acid and merely increasing the spray application pressure. Further, if increased spray pressures are used, the antimicrobial composition can be applied at lower temperatures, potentially resulting in substantial energy savings. Of course there appears to be a relationship between application spray duration and antimicrobial efficacy. While spray durations of as little as about 10 seconds can be used, it has been discovered that a preferred spray duration is from about 10 to about 30 seconds. Without wishing to be limited by theory, the increased antimicrobial efficacy resulting from the use of the higher spray pressures is believed to be due to an improvement in penetrating the surface of the carcass, particularly an increased ability to reach into creases and crevices on the surface of the carcass.

During processing of the carcass meat, the carcasses may also be immersed into a tank containing a quantity of sanitizing solution. The sanitizing solution is preferably agitated to increase the efficacy of the solution and the speed in which the solution kills micro-organisms attached to the carcasses. Agitation can be obtained through conventional means including through ultrasonic means, aeration by bubbling air through the solution or by mechanical means, such as strainers, paddles, brushes, or pump driven liquid jets. The sanitizing solution may also be heated to increase the efficacy of the solution in killing micro-organisms. It is preferable that the carcasses be immersed in the sanitizing solution after the carcasses have been eviscerated and before any cooling process such as a chiller tank or a chill water spray.

In another alternative embodiment of the present invention, the carcasses may be treated with a foaming version of the composition. The foam may be prepared by mixing foaming surfactants with the sanitizing solution at time of use. The foaming surfactants could be nonionic, anionic or cationic in nature. Examples of useful surfactant types include, but not limited to the following: alcohol ethoxylates, alcohol ethoxylate carboxylate, amine sarcosines, alkyl sulfates, alkyl ether sulfate, sulfonates, quaternary ammonium compounds, alkyl sarcosines, betaines and alkyl amides. The foaming surfactant is mixed at time of use with the sanitizing solution. Use solution levels of the foaming agents is from about 50 ppm to about 2.0 wt-%. At time of use, compressed air is injected into the mixture, then applied to the carcass surface through a foam application device such as a tank foamier or an aspirated wall mounted foamer.

In another alternative embodiment of the present invention, the carcasses may be treated with a thickened or gelled version of the composition. In the thickened or gelled state the sanitizing solution remains in contact with the carcass surface for longer periods of time, thus increasing the antimicrobial efficacy. The thickened or gelled solution will also adhere to vertical surfaces. The composition or the sanitizing solution may be thickened or gelled using existing technologies such as: xantham gum, polymeric thickeners, cellulose thickeners or the like. Rod micelle forming systems such as amine oxides and anionic counter ions could also be used. The thickeners or gel forming agents can be used either in the concentrated product or mixing with the sanitizing solution, at time of use. Typical use levels of thickeners or gel agents range from about 100 ppm to about 10 wt-%.

In another alternative embodiment of the present invention, the carcasses may be treated with an electrostatically charged spray of the sanitizing solution. The sanitizing solution can be spray applied as a charged droplets by using conventional electrostatic spray technologies including inductively charged methodologies. As charged droplets, the sanitizing solution will be attracted to opposite or differentially charged surfaces such as the surface of the carcass. As a result, more sanitizing solution will be applied to the carcass surface and less solution will miss the intended target, commonly called over-spray. The charged droplets will also provide an evenly distributed solution layer on the carcass surface. The charged droplet size will range from about 10 microns about 500 microns.

In another alternative embodiment of the present invention, the carcasses may be subjected to a vacuum treatment either before applying the sanitizing solution, during the application of the sanitizing solution or after applying the sanitizing solution. When the carcass is subjected to a vacuum treatment in conjunction with the application of the sanitizing solution, the penetration of the sanitizing solution into the carcass substructure is enhanced. As a result, antimicrobial efficacy is improved. The amount of vacuum utilized is from about 2 inches of Mercury ("Hg) to about 29 inches of Mercury ("Hg).

In another alternative embodiment of the present invention, the carcasses may be subjected to an activating light source following application of the sanitizing solution. The activating light can improve the antimicrobial efficacy of the sanitizing solution. The light source can be ultraviolet, infrared or from the visible spectrum.

The antimicrobial or sanitizing step can optionally be combined with a thermal intervention process which occurs either before, during or after the application of the antimicrobial composition. The thermal intervention process may employ hot water or dry heat. In the case of a hot water thermal process, the carcass is enclosed in a chamber at atmospheric pressure. The chamber is filled with condensing steam (finely divided liquid water) for a short duration, quickly vented, then cooled to prevent browning of the meat carcass. The duration of the steam thermal process may be from about 5 seconds to about 30 seconds. The chamber temperature may reach from about 50° C. to about 93° C. Similarly with dry heat, the carcass is placed in a chamber into which heated air is directed. The air is heated from about 65° C. to about 260° C. The carcass is allowed from about 5 to about 30 seconds contact time with the heated air, the chamber is vented and the carcass is cooled.

Working Examples

The invention will now be described in more detail by reference to the following working examples. The only proper construction of these examples is as nonlimiting, illustrative example showing various formulations, stabilities, and applications of the invention.

Test Formula #1

| Material | Weight Percent |
|---|---|
| Deionized water | 53.9 |
| Mixed Peroxycarboxylic acids[1] | 4.75 |
| Hydrogen Peroxide | 6.9 |
| Acetic Acid | 25.0 |
| Octanoic Acid | 3.5 |
| Hydroxyethylidene-1,1-diphosphonic acid | 0.95 |
| Sodium Octane mixed Mono-and Di-Sulfonate | 5.0 |

[1]A mixture of peroxy acetic and peroxyoctanoic acids is used. After application the composition is maintained in situ as a mixture of acid and peracid through the action of the $H_2O_2$.

Working Example #1

The objective of working example #1 was to determine if 0.5% and 1.0% lactic acid alone and in combination with Test Formula #1 and/or steam achieved a reduction in the bacterial flora present on prerigor beef samples. An exposure time of 10 minutes was utilized for all applications and testing was performed at 33° C.

Operating Procedure:

Sixteen prerigor beef samples were obtained and kept in a cooler until time of testing. Samples were aseptically divided in half. Eight different test treatments were utilized with four replicate pieces per treatment with the exception of the steam +0.5% lactic acid treatment which only had three replicate pieces. Two cores (4.3 cm diameter) were taken from each replicate piece before and after treatment, combined into 99 mL of Phosphate Buffered Dilution water, stomached for 1 minutes and then serially diluted and plated using pour plate technique.

Test Products:
1. Test Formula #1 at 200 ppm Total Peracid
2. Test Formula #1 at 200 ppm Total Peracid+0.5% Lactic Acid
3. Test Formula #1 at 200 ppm Total Peracid+1.0% Lactic Acid
4. 0.5% Lactic Acid
5. Steam Alone, followed by a sterile water rinse
6. Steam+Test Formula #1 at 200 ppm Total Peracid, followed by a sterile water rinse
7. Steam+Test Formula #1 at 200 ppm Total Peracid+0.5% Lactic Acid, followed by a sterile water rinse
8. Steam+0.5% Lactic Acid followed by a sterile water rinse

| Peracid Product Titrated | Actual Titrated Peracid |
|---|---|
| Test Formula #1 at 200 ppm | 212 ppm |
| 200 ppm Test Formula #1 + 0.5% Lactic Acid | 220 ppm |
| 200 ppm Test Formula #1 + 1.0% Lactic Acid | 192 ppm |
| Test Formula #1 + Steam | 210 ppm |
| Test Formula #1 + 0.5% Lactic Acid + Steam | 220 ppm |

Product Application: All product use solutions were applied by a spray application for 10 seconds. This delivered approximately 150 mL of product. An exposure time of 10 minutes was utilized, followed by a 10 second sterile water rinse, if applicable.

Neutralizer: 99 mL of Phosphate Buffered Dilution Water
Dilutions Plated: $10^0$, $10^{-1}$, $10^{-2}$ for Total Plate Count Before
$10^0$, $10^{-1}$ for Total Plate Count After
Plating Medium: Tryptone Glucose Extract Agar
Incubation: 26° C. for 72 hours

Steam Application Parameters

| Test Product Application | Observations |
|---|---|
| Steam Alone | 1st Replicate: Starting temperature was 86° C., ending at 92° C.. A 17 second exposure time was utilized and a 10 second delay occurred prior to the sterile water rinse for 10 seconds. |
| | 2nd Replicate: Starting temperature was high 80° C., ending at 90+° C.. |
| | 3rd & 4th Replicates: Starting temperature was 82° C., ending at 87° C.. An 8 second exposure time and a 10 second sterile water rinse were utilized for replicates 2, 3 and 4. |
| Test Formula | 1st Replicate: Starting temperature was 82° C., ending at 87° C.. |
| | 2nd Replicate: Starting temperature was 80° C., ending at 84° C.. |
| #1 + Steam | 3rd Replicate: Starting temperature was 83° C., ending at 88° C.. |
| | 4th Replicate: Starting temperature was 86° C., ending at 89° C.. |
| | An 8 second exposure time and a 10 second sterile water rinse were utilized for all replicates. |
| Test Formula #1 + 0.5% Lactic Acid + Steam | 1st Replicate: Starting temperature was 88° C., ending at 91.5° C.. |
| | 2nd Replicate: Starting temperature was 86.7° C., ending at 90+?° C.. |
| | 3rd and 4th Replicates: Temperatures were not recorded. An 8 second exposure time and a 10 second sterile water rinse utilized for all replicates. |
| Lactic Acid + Steam | 1st Replicate: Starting temperature was 84° C., ending at 88° C.. |
| | 2nd Replicate: Starting temperature was not recorded, however the ending temperature was 91° C.. |
| | 3rd Replicate: Temperatures were not recorded. An 8 second exposure time and a 10 second sterile water rinse were utilized for all replicates. |

Total Plate Count Results

| Product Application | Average CFU/100 mL Before | Avg. CFU/100 mL After | Avg. $Log_{10}$ Reduc. |
|---|---|---|---|
| Test Formula #1 at 200 ppm | $3.3 \times 10^4$ | $7.7 \times 10^3$ | .80 |
| Test Formula #1 at 200 ppm + 0.5% Lactic Acid | $2.0 \times 10^5$ | $1.7 \times 10^4$ | 1.08 |
| Test Formula #1 at 200 ppm + 1.0% Lactic Acid | $4.4 \times 10^4$ | $1.2 \times 10^3$ | 1.31 |
| 0.5% Lactic Acid | $2.7 \times 10^4$ | $5.4 \times 10^3$ | 0.91 |
| Steam Alone with Sterile Water Rinse | $1.2 \times 10^4$ | $2.4 \times 10^3$ | 1.10 |
| Steam + Test Formula #1 at 200 ppm with Sterile Water Rinse | $1.5 \times 10^4$ | $8.4 \times 10^2$ | 1.51 |
| Steam + Test Formula #1 at 200 ppm + 0.5% Lactic Acid With Sterile Water Rinse | $3.1 \times 10^5$ | $2.6 \times 10^3$ | 2.55 |
| Steam + 0.5% Lactic Acid with Sterile Water Rinse | $2.5 \times 10^4$ | $9.3 \times 10^2$ | 1.69 |

Conclusions

The application of Steam with Test Formula #1 at 200 ppm in combination with 0.5% Lactic Acid outperformed all other treatments by achieving an average of a 2.55 $log_{10}$ reduction on the surface of prerigor meat. Steam alone, provided an average 1.10 $log_{10}$ reduction with temperatures ranging from 80-92° C. Test Formula #1 at 200 ppm in combination with 0.5% Lactic Acid only provided an average 1.10 $log_{10}$ reduction in comparison to an average 1.31 $log_{10}$ reduction in combination with 1.0% Lactic Acid.

The purpose of the remaining working examples was to determine if the use of higher spray pressures, particularly those above 100 psi, would increase the antimicrobial efficacy of the compositions of the invention.

Working Example #2

The objective of the testing was to determine the efficacy of various antimicrobial treatments with extended spray and exposure times against the bacterial flora of prerigor beef.
Test Method/Parameters:
Prerigor beef samples were obtained and kept in a cooler at ambient temperature until time of testing. Ten different test treatments were utilized with four replicates per treatment. Two cores (4.3 cm diameter) were taken as each replicate from one piece for both before- and after-treatment samples and combined into 99 mL of Letheen Broth. The cores/neutralizer mixtures were stomached for 1 minute and then serially diluted and plated using pour plate technique.
Test Products:
Test Formula #1* at 200 ppm Peracid=0.42% (4.2 mL were added to 995.8 mL tap water)
Test Formula #1* at 500 ppm Peracid (10.5 mL were added to 989.5 mL tap water)
0.5% Lactic Acid
*Test Formula #1, batch # Si120972, was titrated at 4.76% total peracid.
Application: Eight cores (2 cores per replicate) were placed onto a clean and sanitary screen. The cores were sprayed with the appropriate test product utilizing a 10- or 30-second spray application time. For each replicate, two cores were removed after a 10-minute exposure time and placed into a stomacher bag containing 99 mL of neutralizer.
Neutralizer: 99 mL Letheen Broth
Dilutions: $10^0$, $10^{-1}$, $10^{-2}$ for Total Plate Count Before
$10^0$, $10^{-1}$ for Total Plate Count After
Plating Medium: Tryptone Glucose Extract Agar
Incubation: 26° C. for 72 hours
Calculations: Average CFU/plate=(All eight counts from four replicates/4)
Average CFU/plate×100=Average CFU/100 mL=Y $$\text{Average} \frac{CFU}{cm^2} = \frac{Y}{2\pi r^2}$$

Dilution=10, 100, or 1000
r=2.15 cm
2=# of cores

| Product Application | Average CFU/ 100 mL Before | Avg. CFU/ 100 mL After | Avg. Log$_{10}$ Reduc. |
|---|---|---|---|
| Water Control 98° F. 25 psi pressure, 10 sec. spray | $3.6 \times 10^4$ | $4.7 \times 10^4$ | 0.05 |
| Water Control 120° 50 psi pressure, 30 sec. spray | $1.2 \times 10^5$ | $1.9 \times 10^5$ | −0.21 |
| 0.5% Lactic Acid 98° F. 25 psi pressure, 10 sec spray | $1.6 \times 10^4$ | $1.5 \times 10^4$ | −0.01 |
| 0.5% Lactic Acid 120° F. 25 psi pressure, 10 sec. spray | $1.0 \times 10^5$ | $8.4 \times 10^4$ | 0.07 |
| Test Formula #1 at 200 ppm Peracid 90° F. 50 psi pressure, 10 sec spray | $2.3 \times 10^4$ | $8.7 \times 10^3$ | 0.41 |
| Test Formula #1 at 200 ppm Peracid 120° F. 50 psi pressure, 10 sec spray | $1.5 \times 10^5$ | $1.6 \times 10^4$ | 0.97 |
| Test Formula #1 at 200 ppm Peracid 120° F. 50 psi pressure, 30 sec spray | $9.0 \times 10^4$ | $3.9 \times 10^4$ | 0.37 |
| Test Formula #1 at 200 ppm Peracid 120° 25 psi pressure, 30 sec spray | $6.5 \times 10^5$ | $6.4 \times 10^5$ $1.9 \times 10^{4*}$ | 0.01 1.65* |
| Test Formula #1 at 500 ppm Peracid 98° F. 25 psi pressure, 30 sec. spray | $4.5 \times 10^4$ | $5.3 \times 10^3$ | 0.93 |
| Test Formula #1 at 500 ppm Peracid 120° F. 25 psi pressure, 10 sec. spray | $4.9 \times 10^4$ | $1.1 \times 10^4$ | 0.67 |

*Average and Log$_{10}$ Reduction not including replicate #3

Conclusions

Overall, highest reductions in the bacteria flora on the surface of prerigor beef were seen with the following treatments:

Test Formula #1 at 200 ppm total peracid at 50 psi pressure with a 10-second spray time at 120° F. achieved an average 0.97 log$_{10}$ reduction.

Test Formula #1 at 500 ppm total peracid at 25 psi pressure with a 30-second spray at 98° F. achieved an average 0.93 log$_{10}$ reduction.

In regard to temperature, 120° F. resulted in higher efficacy with Test Formula #1 at 200 ppm total peracid at 50 psi pressure with a 10-second spray time, with a 0.97 log$_{10}$ reduction versus a 0.41 log$_{10}$ reduction at 98° F.

Working Example #3

The objective of the testing was to determine the efficacy of Test Formula #1 at 200 ppm total peracid with a high pressure application spray at 100° F. against the bacterial flora of prerigor beef.
Test Method/Parameters:
Prerigor beef samples were obtained and kept cooler at ambient temperature until time of testing. Four different test treatments were utilized with four replicates per treatment. Two cores (4.3 cm diameter) were taken as each replicate from one piece for both before and after treatment samples and combined into 99 mL of Letheen Broth. The cores/neutralizer mixtures were stomached for 1 minute and then serially diluted and plated using pour plate technique.
Test Product: Test Formula #1 at 200 ppm total peracid (Batch # Si120972, was titrated at 4.76% total peracid)
Application: Eight cores (2 cores per replicate) were aseptically removed from sample before treatment. These were used for the before treatment samples. The remaining sample was placed onto a clean and sanitary screen. The sample was then sprayed with Vortex at approximately 200 ppm total peracid utilizing a 5-, 10- or 30-second spray application time. For each replicate, two cores were removed after a 10-minute exposure time and placed into a stomacher bag containing 99 mL of neutralizer.

Neutralizer: 99 mL Letheen Broth
Dilutions Plated: $10^0$, $10^{-1}$, $10^{-2}$ for Total Plate Count Before
$10^0$, $10^{-1}$ for Total Plate Count After
Plating Medium: Tryptone Glucose Extract Agar
Incubation: 26° C. for 72 hours
Calculations: Average CFU/plate=(All eight counts from four replicates/4)
Average CFU/plate×100=Average CFU/100 mL=Y $$\text{Average} \frac{CFU}{cm^2} = \frac{Y}{2\pi r^2}$$

Dilution=10, 100, or 1000
r=2.15 cm
2=# of cores

| Product Application | Average CFU/100 mL Before | Avg. CFU/100 mL After | Avg. Log$_{10}$ Reduc. |
|---|---|---|---|
| Water Control ~230 psi pressure, 30 sec. spray | 5.6 × 10$^5$ | 2.7 × 10$^4$ | 1.31 |
| Test Formula #1 at 200 ppm Peracid ~230 psi pressure, 10 sec spray | ~1.9 × 10$^6$ | ~2.0 × 10$^5$ | ~0.96 |
| Test Formula #1 at 200 ppm Peracid ~230 psi pressure, 5 sec spray | ~2.8 × 10$^6$ | 2.0 × 10$^5$ | 1.15 |
| Test Formula #1 at 200 ppm Peracid ~230 psi pressure, 30 sec spray | 2.1 × 10$^6$ | <100 | >2.90 |

Conclusions

Test Formula #1 at 200 ppm peracid with a 30-second exposure time utilizing a high-pressure spray of 230 psi at the nozzle with a distance of approximately 75 cm achieved the highest reduction with <3.4 CFU/cm$^2$ surviving after a 10-minute exposure time at ~110° F. Utilizing this procedure, a >2.90 log reduction was achieved.

Working Example #4

The objective of the testing was to determine the efficacy of Test Formula #1 at approximately 50, 100 and 200 ppm total peracid with a high pressure application spray at elevated temperatures in comparison to Lactic Acid against the bacterial flora of prerigor beef.
Test Method Parameters:
Prerigor beef samples were obtained and kept in a cooler at ambient temperature until time of testing. Four different test treatments were utilized with four replicates per treatment. Two cores (4.3 cm diameter) were taken as each replicate from one piece for both before- and after-treatment samples and combined into 99 mL of Letheen Broth. The cores/neutralizer mixtures were stomached for 1 minute and then serially diluted and plated using pour plate technique.
Test Product: Test Formula #1 at 50, 100 and 200 ppm total peracid
  Lactic Acid (88% concentrate)
  (Batch # Si120972, was titrated at 4.76% total peracid)
Application: Eight cores (2 cores per replicate) were aseptically removed from each sample before treatment. These were used for the before-treatment samples. The remaining sample was placed onto a clean and sanitary screen. The sample was then sprayed with Test Formula #1 at approximately 50, 100 or 200 ppm total peracid utilizing a 20- or 30-second spray application time. 0.5% Lactic Acid utilized only the 30-second spray application. For each replicate, two cores were removed after a 10-minute exposure time and placed into a stomacher bag containing 99 mL of neutralizer.
Neutralizer: 99 mL Letheen Broth
Dilutions: $10^0$, $10^{-1}$, $10^{-2}$ for Total Plate Count Before
$10^0$, $10^{-1}$ for Total Plate Count After
Plating Medium: Tryptone Glucose Extract Agar
Incubation: 16° C. for 72 hours
Calculations: Average CFU/plate=(All eight counts from four replicates/4)
Average CFU/plate×100=Average CFU/100 mL=Y $$\text{Average} \frac{CFU}{cm^2} = \frac{Y}{2\pi r^2}$$

Dilution=10, 100 or 10000
r=2.15 cm
2=# of cores

| Product Application | Average CFU/ 100 mL Before | Avg. CFU/ 100 mL After | Avg. Log$_{10}$ Reduc. |
|---|---|---|---|
| Test Formula #1 at 200 ppm Peracid ~230 psi pressure, 30 sec. spray | 3.7 × 10$^4$ | <100 | >2.58 |
| Test Formula #1 at 200 ppm Peracid ~230 psi pressure 20 sec. spray | 3.1 × 10$^5$ | 3.3 × 10$^3$ | 2.00 |
| Test Formula #1 at 100 ppm Peracid ~230 psi pressure, 30 sec. spray | 1.3 × 10$^6$ | 7.9 × 10$^3$ | 2.22 |
| Test Formula #1 at 100 ppm Peracid ~230 psi pressure 20 sec. spray | 2.0 × 10$^5$ | 4.3 × 10$^2$ | 2.66 |
| Test Formula #1 at 50 ppm Peracid ~230 psi pressure, 30 sec spray | 3.1 × 10$^5$ | 6.3 × 10$^3$ | 1.70 |
| Test Formula #1 at 200 ppm Peracid ~65 psi pressure 30 sec. spray | 2.1 × 10$^5$ | 8.7 × 10$^4$ | 0.38 |
| ~0.5% Lactic Acid ~230 psi pressure, 30 sec. spray | 8.7 × 10$^5$ | 2.3 × 10$^4$ | 1.58 |

Conclusions

Test Formula #1 at 200 ppm total peracid sprayed for 30 seconds at ~230 psi pressure achieved the highest reduction of bacteria present on the surface of prerigor meat with a >2.58 log$_{10}$ reduction. Test Formula #1 at 200 ppm sprayed for 30 seconds at ~65 psi pressure only achieved an average 0.38 log$_{10}$ reduction.

Working Example #5

The objective of the testing was to determine the efficacy of Test Formula #1 and Lactic Acid against *Listeria innocua* ATCC 33090 with a high-pressure application spray at elevated temperatures.
Test Method/Parameters:
Prerigor beef samples were obtained and kept in a cooler at ambient temperature until time of testing. Samples were cut into 13 cm pieces and 2.0 mL of the inoculum (see Test System Preparation below) was spread evenly over the entire surface of the sample. Inoculated samples were then left at room temperature (~23° C.) for ≥15 minutes. Four replicate samples were taken (two cores per replicate) before treatment. After each spray treatment, a 10-minute exposure time was utilized, and taken four replicate samples were taken (two cores per replicate) and stomached for 1 minute, serially diluted and plated using pour plate technique.

Treatments:
1. Test Formula #1 at 200 ppm total peracid with ~psi pressure spray, 30 second spray time.
2. Test Formula #1 at 200 ppm total peracid with ~150 psi pressure spray, 30 second spray time.
3. Test Formula #1 at 200 ppm total peracid with ~100 psi pressure spray, 30 second spray time.
4. Water Control with ~220 psi pressure spray, 30-second spray time.
5. ~0.5%-0.75% Lactic Acid with ~220 psi pressure spray, 30-second spray time.
6. Test Formula #1 at 100 ppm total peracid with ~220 psi pressure spray, 30 second spray time.
7. Test Formula #1 at 200 ppm total peracid with ~220 psi pressure spray, 15 second spray time.

*Tiration of the Lactic Acid solution used 12 drops of Sodium Hydroxide for the indicator color change. In preliminary titrations of a 0.5% Lactic Acid solution, 7 drops of 1N Sodium Hydroxide were needed. Therefore, the sample was estimated to be at a concentration between 0175% and 1.0% Lactic Acid.

Test Temperature: ~120° F.
Test System: *Listeria innocua* ATCC 33090
Test System Preparation: 25 grams of sterilized cow feces was added into 50 grams of sterile phosphate buffered dilution water and stomached for 1 minute. 60.0 grams from this fecal slum was transferred to a sterile stomacher bag and 6.0 mL of an ~$10^8$ CFU/mL *Listeria innocua* 24-hour broth culture (grown in BHI broth at 37° C.) was added and mixed. This inoculum was therefore estimated at $10^7$ CFU/mL, which yielded approximately $10^5$ CFU/cm$^2$.

Exposure Time: 10 minutes
Neutralizer: 99 mL Letheen Broth
Dilutions: $10^{-4}$, $10^{-5}$, $10^{16}$ (for Before Treatment, Inoculation Numbers samples)
$10^0$, $10^{-1}$, $10^{-2}$ (After Treatment samples)
Plating Medium: *Listeria* Selective Agar
Incubation: 26° for 72 hours
Calculations: Average CFU/plate=(All eight counts from four replicates/4)
Average CFU/plate×100=Average CFU/100 mL=Y $$\text{Average} \frac{CFU}{cm^2} = \frac{Y}{2\pi r^2}$$

r=2.15 cm 2=# of cores

| Product Application | Avg. CFU/ 100 mL After | Avg. Log$_{10}$ Reduc. |
|---|---|---|
| Test Formula #1 at 200 ppm Peracid ~220 psi pressure 30 second spray* | 1.6 × 10$^5$ | 1.97 |
| Test Formula #1 at 200 ppm Peracid ~150 psi pressure 30 second spray* | 5.1 × 10$^4$ | 2.45 |
| Test Formula #1 at 200 ppm Peracid ~100 psi pressure 30 second spray* | 1.4 × 10$^5$ | 2.03 |
| Water Control ~220 psi pressure 30 second spray | 4.9 × 10$^5$ | 1.48 |
| Lactic Acid ~220 psi pressure 30 second spray | 3.5 × 10$^5$ | 1.63 |
| Test Formula #1 at 100 ppm Peracid ~220 psi pressure 30 second spray* | 1.6 × 10$^5$ | 1.97 |
| Test Formula #1 at 200 ppm Peracid ~100 pressure 15 second spray* | 2.2 × 10$^5$ | 1.83 |

Conclusions

Treatment 200 ppm peracid with an ~150 psi spray for 30 seconds achieved an average 2.45 log$_{10}$ reduction of *Listeria innocua* ATCC 33090. Lactic Acid achieved a 1.63 log$_{10}$ reduction of this organism which was only slightly higher than the water control which achieved an average 1.48 log$_{10}$ reduction.

The above discussion, examples, and data illustrate our current understanding of the invention. However, since many variations of the invention can be made without departing from the spirit and scope of the invention, the invention resides in the claims hereinafter appended.

The invention claimed is:

1. A method of treating an animal carcass to reduce a microbial population in resulting cut meat, the method comprising:
   diluting a concentrated antimicrobial composition, wherein the concentrated antimicrobial composition comprises:
   (1) about 20% to about 50% acetic acid, and at least about 0.5% peracetic acid (PAA), or
   (2) at least about 0.5% acetic acid, and about 0.5% to about 20% peracetic acid (PAA); and
   treating the carcass with the diluted antimicrobial composition for at least about 10 seconds, the diluted antimicrobial composition comprising:
   (i) at least about 2 parts per million (ppm) of one or more mono- or di-peroxycarboxylic acids having up to 12 carbon atoms;
   (ii) at least about 20 ppm of one or more carboxylic acids having up to 18 carbon atoms,
   thereby reducing the microbial population by at least one log$_{10}$ reduction.

2. The method of claim 1, wherein the treatment does not induce a deleterious organoleptic effect.

3. The method of claim 1, wherein the population reduction comprises at least two log$_{10}$ reduction in the microbial population.

4. The method of claim 1, wherein the population reduction comprises at least three log$_{10}$ reduction in the microbial population.

5. The method of claim 1, wherein the population comprises a human pathogen.

6. The method of claim 1, wherein the population comprises *Escherichia coli*.

7. The method of claim 1, wherein the carcass is a muscle meat.

8. The method of claim 7, wherein the muscle meat is selected from the group consisting of beef, pork, veal, buffalo, and lamb.

9. The method of claim 1, wherein the carcass is sea food.

10. The method of claim 9, wherein the sea food is selected from the group consisting of scallops, shrimp, crab, octopus, mussels, squid, and lobster.

11. The method of claim 1, wherein the carcass is poultry.

12. The method of claim 11, wherein the poultry is selected from the group consisting of chicken, turkey, ostrich, game hen, squab, and pheasant.

13. The method of claim 1, wherein the concentrated antimicrobial composition comprises about 20% to about 50% acetic acid and about 0.5% to about 20% peracetic acid (PAA).

14. The method of claim 1, wherein the concentrated antimicrobial composition comprises about 0.5% to about 60% acetic acid and about 0.5% to about 20% peracetic acid (PAA).

15. The method of claim 14, wherein the concentrated antimicrobial composition comprises about 10% to about 60% acetic acid and about 0.5% to about 20% peracetic acid (PAA).

16. The method of claim 1, wherein the concentrated antimicrobial composition further comprises an oxidizer.

17. The method of claim 16, wherein the oxidizer is hydrogen peroxide, and the concentrated antimicrobial composition comprises about 1% to about 35% hydrogen peroxide, or at least about 5% hydrogen peroxide.

18. The method of claim 1, wherein the concentrated antimicrobial composition further comprises about 0.01% to about 10% of a sequestrant, about 0.1% to about 20% of a hydrotrope, and/or about 0.01% to about 10% of a thickening or gelling agent.

19. The method of claim 1, wherein the diluted antimicrobial composition comprises between about 10 ppm and about 500 ppm of peracetic acid.

20. The method of claim 1, wherein the diluted antimicrobial composition comprises between about 10 ppm and about 500 ppm of one or more mono- or di-peroxycarboxylic acids selected from the group consisting of peroxyformic acid, peroxyacetic acid, peroxypropionic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, and peroxydodecanoic acid.

21. The method of claim 1, wherein the diluted antimicrobial composition comprises between about 20 ppm and about 10,000 ppm of acetic acid.

22. The method of claim 1, wherein the diluted antimicrobial composition comprises between about 20 ppm and about 10,000 ppm of one or more carboxylic acids having up to 18 carbon atoms selected from the group consist of formic acid, acetic acid, propionic acid, butanoic acid, pentanoic acid, hexanoic acid, heptanoic acid, octanoic acid, nonanoic acid, decanoic acid, undecanoic acid, dodecanoic acid, lactic acid, maleic acid, ascorbic acid, citric acid, hydroxyacetic acid, neopentanoic acid, neoheptanoic acid, neodecanoic acid, oxalic acid, malonic acid, succinic acid, glutaric acid, adipic acid, pimelic acid, and subric acid.

23. The method of claim 1, wherein said diluted antimicrobial composition comprises about 2 to 25 parts by weight of hydrogen peroxide per each one million parts of the composition.

24. The method of claim 1, wherein the diluted antimicrobial composition is applied to the carcass by means of a spray, a fog, or a foam, or in the form of a thickened or gelled solution.

25. The method of claim 24, wherein the diluted antimicrobial composition is applied by means of an electrostatically accelerated spray.

26. The method of claim 24, wherein the diluted antimicrobial composition is sprayed onto the carcass at a pressure of at least about 50 psi at a temperature of up to about 60° C. resulting in a contact time of at least about 30 seconds.

27. The method of claim 1, wherein the carcass is immersed or dipped in the diluted antimicrobial composition.

28. The method of claim 27, the method further comprising agitating the diluted antimicrobial composition.

29. The method of claim 1, wherein the pH of the diluted antimicrobial composition is from about 1 to about 11.

30. The method of claim 29, wherein the pH is from about 2 to about 10.

* * * * *